US010278922B2

(12) United States Patent
Anderson et al.

(10) Patent No.: US 10,278,922 B2
(45) Date of Patent: *May 7, 2019

(54) HYDROGEL ENCAPSULATED CELLS AND ANTI-INFLAMMATORY DRUGS

(71) Applicants: Massachusetts Institute of Technology, Cambridge, MA (US); The Children's Medical Center Corporation, Boston, MA (US)

(72) Inventors: Daniel G. Anderson, Framingham, MA (US); Robert S. Langer, Newton, MA (US); Tram T. Dang, Cambridge, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/831,570

(22) Filed: Dec. 5, 2017

(65) Prior Publication Data

US 2018/0092850 A1    Apr. 5, 2018

Related U.S. Application Data

(63) Continuation of application No. 13/400,382, filed on Feb. 20, 2012, now Pat. No. 9,867,781.

(60) Provisional application No. 61/444,206, filed on Feb. 18, 2011.

(51) Int. Cl.
| | |
|---|---|
| *A61K 9/16* | (2006.01) |
| *A61K 9/00* | (2006.01) |
| *A61K 31/573* | (2006.01) |
| *A61K 45/06* | (2006.01) |
| *A61K 35/39* | (2015.01) |
| *G01N 33/50* | (2006.01) |
| *A61L 27/38* | (2006.01) |
| *A61L 27/48* | (2006.01) |
| *A61L 27/52* | (2006.01) |
| *A61L 27/54* | (2006.01) |
| *C12N 5/071* | (2010.01) |

(52) U.S. Cl.
CPC .......... *A61K 9/1641* (2013.01); *A61K 9/0019* (2013.01); *A61K 31/573* (2013.01); *A61K 35/39* (2013.01); *A61K 45/06* (2013.01); *A61L 27/3804* (2013.01); *A61L 27/48* (2013.01); *A61L 27/52* (2013.01); *A61L 27/54* (2013.01); *C12N 5/0676* (2013.01); *G01N 33/5088* (2013.01); *A61L 2300/41* (2013.01); *A61L 2300/622* (2013.01); *A61L 2300/64* (2013.01); *C12N 2502/1157* (2013.01); *C12N 2533/40* (2013.01); *C12N 2533/74* (2013.01)

(58) Field of Classification Search
CPC .... A61K 9/1641; A61K 35/39; A61K 31/573; A61K 45/06; A61K 9/0019; C12N 5/0676; C12N 2502/1157; C12N 2533/74; C12N 2533/40; A61L 27/3804; A61L 27/52; A61L 27/54; A61L 27/48; A61L 2300/622; A61L 2300/41; A61L 2300/64; G01N 33/5088

See application file for complete search history.

(56) References Cited

U.S. PATENT DOCUMENTS

| | | |
|---|---|---|
| 4,352,883 A | 10/1982 | Lim |
| 4,391,909 A | 7/1983 | Lim |
| 4,407,967 A | 10/1983 | Lim |
| 4,409,331 A | 10/1983 | Lim |
| 4,673,566 A | 6/1987 | Goosen |
| 4,689,293 A | 8/1987 | Goosen |
| 4,744,933 A | 5/1988 | Rha |
| 47,496,208 | 6/1988 | Rha |
| 4,806,355 A | 2/1989 | Goosen |
| 5,427,935 A | 6/1995 | Wang |
| 2011/0111033 A1 | 5/2011 | Stover et al. ................. 424/487 |

FOREIGN PATENT DOCUMENTS

WO    wo2011005381 a2    1/2011

OTHER PUBLICATIONS

Su et al., Biomaterials 31 (2010) 308-314.
Baruch et al., Biomed Microdevices (2009) 11:1103-1113.
Sun et al., Am. Soc. Gene & Cell Therapy, vol. 18, No. 9, 1606-16-14 (Sep. 2010).
Koch et al. J. Microencapsul. May-Jun. 2003; 20(3):303-16.
Bhardwaj, et al. "PLGA/PVA hydrogel composites for long-term inflammation control following S.C. implantation", Intl J Pharma., 384:78-86 (2010).
Giovagnoli, et al., Bioactive long-term release from biodegradable microspheres preserves implanted ALG-PLO-ALG microcapsules from In Vivo response to purified alginate\, Pharma Res., 27 (2):285-95 (2010).

(Continued)

*Primary Examiner* — Robert S Cabral
(74) *Attorney, Agent, or Firm* — Pabst Patent Group LLP

(57) ABSTRACT

A composition containing biocompatible hydrogel encapsulating mammalian cells and anti-inflammatory drugs is disclosed. The encapsulated cells have reduced fibrotic overgrowth after implantation in a subject. The compositions contain a biocompatible hydrogel having encapsulated therein mammalian cells and anti-inflammatory drugs or polymeric particles loaded with anti-inflammatory drugs. The anti-inflammatory drugs are released from the composition after transplantation in an amount effective to inhibit fibrosis of the composition for at least ten days. Methods for identifying and selecting suitable anti-inflammatory drug-loaded particles to prevent fibrosis of encapsulated cells are also described. Methods of treating a disease in a subject are also disclosed that involve administering a therapeutically effective amount of the disclosed encapsulated cells to the subject.

24 Claims, 9 Drawing Sheets

(56) References Cited

OTHER PUBLICATIONS

Anderson and Shive, et al., "Biodegradation and biocompatibility of PLA and PLGA microspheres", Adv Drug Deliver Rev., 28(1):5-24 (1997).
Anderson, et al., "Foreign body reaction to biomaterials", Semin Immunol 20 (2):86-100 (2008).
Bae, et al., "Effect of temporally controlled release of dexamethasone on in vivo chondrogenic differentiation of mesenchymal stromal cells", J Cont. Rel., 143 (1):23-30 (2010).
Bhardwaj, el al., "Controlling acute inflammation with fast releasing dexamethasone-PLGA microsphere/pva hydrogel composites for implantable devices", J Diabetes Sci Technol 1(1): 8-17 (2007).
Blasi, et al., "Preparation and in vitro and in vivo characterization of composite microcapsules for cell encapsulation", Int J Pharm 324(1):27-36 (2006).
Bratlie, et al., "Rapid biocompatibility analysis of materials via in vivo fluorescence imaging of mouse models", PLoS One 5(4): e10032 (2010).
Bunger, et al., "Deletion of the tissue response against alginate-pll capsules by temporary release of co-encapsulated steroids", Biomaterials 26(15):2353-60 (2005).
Cole, et al., "Microencapsulated islet grafts in the BB/E rat; a possible role for cytokines in graft failure", Diabetologia., 35(3):231-7 (1992).
D\Souza, et al., "Methods to assess in vitro drug release from injectable polymeric particulate systems", Pharma Res 23(3):460-74 (2006).
Dash, et al., "Therapeutic applications of implantable drug delivery systems", J Pharmacol Toxicol 40(1):1-12 (1998).
De Groot, et al., "Causes of limited survival of microencapsulated pancreatic islet grafts", J Surg Res 121(1):141-50 (2004).
De Vos, et al., "Improved biocompatibility but limited graft survival after purification of alginate for microencapsulation of pancreatic islets", Diabetologia 40(3):262-70 (1997).
De Vos, et al., "Tissue responses against immunoisolating alginate-PLL capsules in the immediate posttransplant period", J Biomed Mater Res 62(3):430-437 (2002).
Erfle, et al., "In vivo cellular secretory products might affect the degradation rate of the polymeric matrix", Cardiovasc Pathol 6(6):333-40 (1997).
Faurschou, et al., "Neutrophil granules and secretory vesicles in inflammation", Microbes Infect 5(14):1317-27 (2003).
Field, et al., "Improved islet isolation from rat pancreas using 35% bovine serum albumin in combination with Dextran gradient separation", Transplantation 61:1554 1996).
Granchi, et al., "Silicone breast implants: the role of immune system on capsular contracture formation", J Biomed Mater Res 29(2):197-202 (1995).
Hickey, et al,, "In vivo evaluation of a dexamethasone/PLGA microsphere system designed to suppress the inflammatory tissue response to implantable medical devices", Biomed Mater Res 61(2):180-7 (2002).
Hunt, et al., "Quantifying the soft tissue response to implanted materials", Biomaterials 16(3):167-70 (1995).
Hunt, et al., "Image analysis in the evaluation of biomaterials", J Biomed Eng 15(1):39-45 (1993).
Hunt, et al., "Modification of the soft tissue response to implanted materials through the use of an anti-inflammatory drug", J Mater Sci: Mater Med 3(3):160-9 (1992).
Jain, "The manufacturing techniques of various drug loaded biodegradable poly (lactide-co-glycolide) (PLGA) devices", Biomaterials 21(23):2475-90 (2000).
Ju, et al., "A dexamethasone-loaded PLGA microspheres/collagen scaffold composite for implantable glucose sensors", J Biomed Mater Res 93(1):200-10 (2010).
Kvist, et al., "Biocompatibility of electrochemical glucose sensors implanted in subcutis of pigs", Diabetes Technol 8(4):463-75 (2006).
Labhasetwar, et al., "Implants for site-specific drug delivery", J Appl Blomater 2(3):211-2 (1991).
Labow, et al., "Neutrophil-mediated degradation of segmented polyurethanes", Biomaterials 16(1):51-9 (1995).
Labow, et al., "Human macrophage-mediated biodegradation of polyurethanes: assessment of candidate enzyme activities", Biomaterials 23(19):3969-75 (2002).
Linetsky, et al., "Improved human islet isolation using a new enzyme blend, liberase", Diabetes 46:1120 (1997).
Lominadze, et al., "Proteomic analysis of human neutrophil granules", Mol Cell Proteomics 4(10):1503 (2005).
Morais, et al., "Biomaterials/tissue interactions: possible solutions to overcome foreign body response", AAPS J 12(2):188-96 (2010).
Park, et al., "Biocompatibility issues of implantable drug delivery systems", Pharm Res 13(12):1770-6 (1996).
Park, et al., "Injectable biodegradable hydrogel composites for rabbit marrow mesenchymal stem cell and growth factor delivery for cartilage tissue engineering", Biomat., 28:3217-27 (2007).
Patil, et al., "Dexamethasone-loaded poly(lactio-co-glycolic) acid microspheres/poly(vinyl alcoholz) hydrogel composite coatings for inflammation control", Diab. Tech Thera., 6 (6):887-97 (2004).
Peterson, et al., "Applications of laser scanning cytometry in immunohistochemistry and routine histopathology", Toxicol pathol 36(1):117 (2008).
Remes, et al., "Immune response in biocompatibility", Biomaterials 13 (11):731-43 (1992).
Rhen, et al., "Antiinflammatory action of glucocorticoids—new mechanisms for old drugs", New Engl J Med 353(16):1711-23 (2005).
Ricci, et al., "Ketoprofen controlled release from composite microcapsules for cell encapsulation: effect on post-transplant acute inflammation", J Control Release 107(3):395-407 (2005).
Robitaille, et al., "Inflammatory response to peritoneal implantation of alginate-poly-L-lysine microcapsules", Biomaterials 26(19):4119-4127 (2005).
Sharkawy, et al., "Engineering the tissue which encapsulates subcutaneous implants. I. Diffusion properties", J Biomed Mater Res 37(3):401-12 (1997).
Sharkawy, et al., "Engineering the tissue which encapsulates subcutaneous implants. II. Plasma-tissue exchange properties", J Biomed Mater Res 40 (4):586-97 (1998).
Singarayar, et al., "A comparative study of the action of dexamethasone sodium phosphate and dexamethasone acetate in steroid-eluting pacemaker leads", PACE 28(4):311-5 (2005).
Su, et al., "Anti-inflammatory peptide-functionalized hydrogels for insulin-secreting cell encapsulation", Biomat, 31(2):308-14 (2010).
Tuckermann, et al., "Macrophages and neutrophils are the targets for immune suppression by glucocorticoids in contact allergy", J Clin Invest 117(5):1381-90 (2007).
Tung, et al., "In vivo imaging of proteolytic enzyme activity using a novel molecular reporter", Cancer Res 60(17):4953-8 (2000).
Vaithilingam, et al., "Islet transplantation and encapsulation: an update on recent developments", Diabet Stud, 8(1):51-67 (2011).
Van der Giessen, et al., "Marked inflammatory sequelae to implantation of biodegradable and nonbiodegradable polymers in porcine coronary arteries", Circulation 94(7):1690-7 (1996).
Van Schilfgaarde, et al., "Factors influencing the properties and performance of microcapsules for immunoprotection of pancreatic islets", J Mol Med 77(1):199-205 (1999).
Vane, et al., "Anti-inflammatory drugs and their mechanism of action", Inflamm Res 47(14):78-87 (1998).
Ward, et al., "A hook-traction technique for Norplant removal", Obstet Gynecol 86(5):848-50 (1995).
Wei, et al., "Drug-carrier/hydrogel scaffold for controlled growth of cells", Eu J Pharmac Biophatmac., 78:346-54 (2011).
Williams, "On the mechanisms of biocompatibiiity", Biornaterials 29 (20):2941-53 (2008).
Wisniewski, et al., "Characterization of implantable biosensor membrane biofouling", Fresenius J Anal Chem 366(6):611-21 (2000).
Wu, et al., "Drug/device combinations for local drug therapies and infection prophylaxis", Biomaterials 27(11):2450-67 (2006).
Yin, et al., "Microcapsules with improved mechanical stability for hepatocyte culture", Biomaterials, 24:1771-1780 (2003).

(56) References Cited

OTHER PUBLICATIONS

Zhong, et al., "Dexamethasone-coated neural probes elicit attenuated inflammatory response and neuronal loss compared to uncoated neural probes", Brain Res 1148:15-27 (2007).
Zolnik, et al., "Evaluation of in vivo-in vitro release of dexamethasone from PLGA microspheres", J Control Release 127(2):137-45 (2008).

HYDROGEL ENCAPSULATED CELLS AND ANTI-INFLAMMATORY DRUGS

CROSS REFERENCE TO RELATED APPLICATIONS

This application is a continuation of U.S. Ser. No. 13/400,382, filed on Feb. 20, 2012, which claims priority to and benefit of U.S. Provisional Application No. 61/444,206, filed Feb. 18, 2011, which is hereby incorporated herein by reference in its entirety.

FIELD OF THE INVENTION

The invention is generally related to the field of cell encapsulation. More particularly, some aspects of the invention relate to a biocompatible hydrogel encapsulating mammalian cells and polymeric particles loaded with anti-inflammatory drugs.

BACKGROUND OF THE INVENTION

Transplantation of human islet cells can provide good glycemic control in diabetic recipients without exogenous insulin. However, a major factor limiting its application is the recipient's need to adhere to life-long immunosuppression, which has serious side effects. Microencapsulating the human islets is a strategy that should prevent rejection of the grafted tissue without the need for anti-rejection drugs.

However, despite promising studies in various animal models, the encapsulated human islets so far have not made an impact in the clinical setting. Many non-immunological and immunological factors such as biocompatibility, reduced immunoprotection, hypoxia, pericapsular fibrotic overgrowth, effects of the encapsulation process, and post-transplant inflammation hamper the successful application of this promising technology (Vaithilingam V, et al. Diabet Stud, 8(1):51-67 (2011)).

One major challenge to clinical application of encapsulated cells and other biomaterials and medical devices is their potential to induce a non-specific host response (Williams D F. Biomaterials 29(20):2941-53 (2008); Park H, et al. Pharm Res 13(12):1770-6 (1996); Kvist P H, et al. Diabetes Technol 8(4):463-75 (2006); Wisniewski N, et al. J Anal Chem 366(6):611-21 (2000); Van der Giessen W J, et al. Circulation 94(7):1690-7 (1996); Granchi D, et al. J Biomed Mater Res 29(2):197-202 (1995); Ward C R, et al. Obstet Gynecol 86(5):848-50 (1995); Remes A, et al. Biomaterials 13(11):731-43 (1992)). This reaction involves the recruitment of early innate immune cells such as neutrophils and macrophages, followed by fibroblasts which deposit collagen to form a fibrous capsule surrounding the implanted object (Williams D F. Biomaterials 29(20):2941-53 (2008); Remes A, et al. Biomaterials 13(11):731-43 (1992); Anderson J M, et al. Semin Immunol 20(2):86-100 (2008); Anderson J M, et al. Adv Drug Deliver Rev 28(1):5-24 (1997); Abbas A K, et al. Pathologic Basis of Disease. 7th ed. Philadelphia: W.B Saunders (2009)). Fibrotic cell layers can hinder electrical (Singarayar S, et al. PACE 28(4):311-5 (2005)) or chemical communications and prevent transport of analytes (Sharkawy A A, et al. J Biomed Mater Res 37(3):401-12 (1997); Sharkawy A A, et al. J Biomed Mater Res 40(4):598-605 (1998); Sharkawy A A, et al. J Biomed Mater Res 40(4):586-97 (1998)) and nutrients, thus leading to the eventual failure of many implantable medical devices such as immunoisolated pancreatic islets (De Groot M, et al. J Surg Res 121(1):141-50 (2004); De Vos P, et al. Diabetologia 40(3):262-70 (1997); Van Schilfgaarde R, et al. J Mol Med 77(1):199-205 (1999)).

The incorporation of controlled-release delivery systems of anti-inflammatory drugs into medical devices has been proposed to mitigate host response and improve device durability (Wu P, et al. Biomaterials 27(11):2450-67 (2006); Dash A K, et al. J Pharmacol Toxicol 40(1):1-12 (1998); Labhasetwar V, et al. J Appl Biomater 2(3):211-2 (1991); Morais J M, et al. AAPS J 12(2):188-96 (2010); Hunt J A, et al. J Mater Sci: Mater Med 3(3):160-9 (1992)). This approach has shown promise in a number of clinical applications. For example, controlled elution of steroids from pace-maker leads reduces fibrosis formation and enhances long-term electrical communication between the leads and surrounding cardiac tissue (Singarayar S, et al. PACE 28(4):311-5 (2005)). However, similar attempts to improve the performance of other medical devices such as immunoisolated islets for diabetes therapy have proven challenging (Williams D F. Biomaterials 29(20):2941-53 (2008)).

Researchers developing controlled-release drug formulations to mitigate host response have largely focused on decreasing the number of inflammatory cells infiltrating the host-device interface. However, various factors in the design of controlled-release formulations such as drug selection, drug loading, particle sizes and corresponding release kinetics can dynamically affect a range of biological activities in the host response. The presence of anti-inflammatory drugs may alter not only the quantity and variety of immune cells recruited but also the kinetics of cellular activities such as the secretion of inflammatory enzymes or cell signaling pathways (Vane J R, et al. Inflamm Res 47(14):78-87 (1998); Rhen T, et al. New Engl J Med 353(16):1711-23 (2005)). In vivo cellular secretory products might affect the degradation rate of the polymeric matrix (Erfle D J, et al. Cardiovasc Pathol 6(6):333-40 (1997); Labow R S, et al. Biomaterials 16(1):51-9 (1995); Labow R S, et al. Biomaterials 23(19):3969-75 (2002)) used to encapsulate drugs, and are partly responsible for the discrepancy between in vitro and in vivo release kinetics (Zolnik B S, et al. J Control Release 127(2):137-45 (2008)).

There remains a substantial need to better understand the immunomodulatory effects of anti-inflammatory drugs on the host-tissue biology at the implant site (Wu P, et al. Biomaterials 27(11):2450-67 (2006)). Such knowledge can lead to better design of controlled-release drug delivery systems to improve the biocompatibility of implanted medical devices.

It is an object of the present invention to provide a cell encapsulation system for transplanting cells with reduced pericapsular fibrotic overgrowth.

It is a further object of the invention to provide a cell encapsulation system for transplanting cells that inhibits a cellular immune response.

It is a further object of the invention to provide a method for identifying anti-inflammatory drugs formulations that inhibit inflammation caused by encapsulated cells.

It is a further object of the invention to provide improved methods for treating diabetes using encapsulated islet cells.

SUMMARY OF THE INVENTION

A biocompatible hydrogel encapsulating mammalian cells and anti-inflammatory drugs for transplantation with decreased cellular immune response and/or pericapsular fibrotic overgrowth has been developed. The hydrogel has encapsulated therein one or more mammalian cells and one or more anti-inflammatory drugs dispersed in, on, and/or encapsulated within a biocompatible hydrogel. The anti-inflammatory drug can be dispersed within the hydrogel for quick release, conjugated to the hydrogel by a biodegradable chemical linker, for delayed release, or a combination thereof.

In a preferred embodiment, the one or more anti-inflammatory drugs are present in drug-loaded polymeric particles for controlled release. In some embodiments, the cells and the anti-inflammatory drugs or drug-loaded polymeric particles are encapsulated together in the same biocompatible hydrogel. In other embodiments, the cells and anti-inflammatory drugs or drug-loaded polymeric particles are compartmentalized within the hydrogel. Compartmentalizing the drug to the surface of the hydrogel facilitates outward drug diffusion, maximizes drug interaction with immune cells, and minimizes interference with the mammalian cells inside. Therefore, in preferred embodiments, a hydrogel composition is configured with a core and envelope structure. In these embodiments, the cells are preferably encapsulated in a core hydrogel and the anti-inflammatory drugs or drug-loaded polymeric particles are encapsulated within an envelope hydrogel. In some embodiments, the core and envelope hydrogels are separated by a membrane or shell.

Transplant rejection is an adaptive immune response that occurs via cellular immunity (mediated by killer T cells) as well as humoral immunity (mediated by activated B cells secreting antibody molecules), along with an innate immune response mediated by phagocytic cells and soluble immune proteins. Cellular immunity protects the body by activating antigen-specific cytotoxic T-lymphocytes that are able to induce apoptosis in body cells displaying epitopes of foreign antigen on their surface, activating macrophages and natural killer cells, and stimulating cells to secrete a variety of cytokines that influence the function of other cells involved in adaptive immune responses and innate immune responses. In preferred embodiments, the one or more anti-inflammatory drugs are released from the composition in an amount effective to inhibit cellular immunity at the transplant site for at least 2 weeks, more preferably 3, 4, 5, or 6 weeks.

In some embodiments, the one or more anti-inflammatory drugs are released from the composition in an amount effective to provide spatially localized inhibition of inflammation in the subject for at least 10 days, more preferably 14, 30, 60, or 90 days. In some embodiments, the spatially localized inhibition of inflammation occurs without systemic immunosuppression. In some embodiments, spatially localized inflammation is detected by measuring cathepsin activity at the injection sites in the subject. In other embodiments, spatially localized inflammation is detected by measuring reactive oxygen species (ROS) at the injection sites in the subject. In some embodiments, systemic immunosuppression is detected by measuring no cathepsin activity or ROS at control sites in the subject, e.g., sites injected with drug-free polymeric particle or hydrogel.

In some cases, the one or more anti-inflammatory drugs inhibit pericapsular fibrosis of the composition after administration into the subject by at least 50%, more preferably 60%, 70%, 80%, 90%, or 100%, for at least 10 days, more preferably 14, 30, 60, or 90 days, compared to a drug-free hydrogel. In preferred embodiments, the one or more anti-inflammatory drugs are released from the composition in an amount effective to prevent detectable fibrosis of the composition for at least 30 days, preferably at least 60 days, more preferably at least 90 days.

The hydrogels can be fabricated into any size or shape suitable for cell encapsulation and transplantation. In preferred embodiments, the hydrogels are formed into microcapsules. Microcapsules for encapsulating cells preferably have a mean diameter of about 150 µm to about 1000 µm, more preferably 300 µm to about 750 µm, even more preferably about 200 µm to about 500 µm.

In some embodiments, the compositions are fabricated into a macrodevice. For example, in some embodiments, cells encapsulated in hydrogel are coated onto a surface, such as a planar surface. In some embodiments, microcapsules containing cells are adhered to tissue of a subject using a biocompatible adhesive. In other embodiments, microcapsules containing cells are coated onto a medical device suitable for implantation. In these embodiments, the anti-inflammatory drug or drug-loaded particles may be encapsulated with the cells in the hydrogel. In preferred embodiments, the anti-inflammatory drug or drug-loaded particles are incorporated into the biocompatible adhesive. FIG. 11C illustrates a macrodevice embodiment. As noted in this figure, microcapsules can be molded into desired shapes and geometries, e.g., suitable for engineering 3D tissue constructs and macrodevices (Dang T T, et al. *Biomaterials* 30:6896-6902 (2009)).

The compositions may be fabricated into artificial organs, such as an artificial pancreas containing encapsulated islet cells. In some of these embodiments, the cells are encapsulated in a single hydrogel compartment. In other embodiments, the composition contains a plurality of microencapsulated cells dispersed or encapsulated in a biocompatible structure.

In some embodiments, the anti-inflammatory drugs are present in the compositions as free drug. In other embodiments, the anti-inflammatory drugs are present in drug-loaded polymeric particles. The drug loaded polymeric particles are preferably microparticles or nanoparticles. The mean diameter of the particles may be selected and optimized based on the particular drug, dosage, and release rate needed. In preferred embodiments, the drug loaded polymeric particles are microparticles having a mean diameter of about 1 µm to about 100 µm, preferably about 1 µm to about 50 µm, more preferably 1 µm to about 10 µm. In other embodiments, drug loaded polymeric particles are nanoparticles having a mean diameter of about 10 nm to about 999 nm, preferably at least about 50 nm, more preferably at least about 100 nm, more preferably at least about 500 nm.

Suitable biocompatible hydrogels for cell encapsulation are known and include polysaccharides, polyphosphazenes, poly(acrylic acids), poly(methacrylic acids), copolymers of acrylic acid and methacrylic acid, poly(alkylene oxides), poly(vinyl acetate), polyvinylpyrrolidone (PVP), and copolymers and blends of each. In preferred embodiments, the biocompatible hydrogel is a polysaccharide. Preferred polysaccharides include alginate, chitosan, hyaluronan, and chondroitin sulfate. A particularly preferred hydrogel for cell encapsulation is alginate.

Biocompatible, biodegradable polymers suitable for controlled drug delivery are also known in the art and include polylactic acid (PLA), polyglycolic acid (PGA), poly(lactic-co-glycolic acid) (PLGA), polycaprolactone (PCL), polyhydroxyalkanoate (PHA), poly(lactic acid)-poly(ethylene oxide) (PLA-PEG), polyanhydrides, poly(ester anhydrides), polymethylmethacrylate [PMMA], poly(2-hydroxyethyl methacrylate) [pHEMA], polycaprolactone [PCL], cellulose acetate, chitosan, and copolymers and blends thereof. A particularly preferred polymer for controlled delivery of anti-inflammatory drugs from hydrogels is poly(lactic-co-glycolic acid) (PLGA).

Suitable shell materials for separating hydrogel polymers include polycation. In preferred embodiments, the polycation is a polycationic polymer such as polylysine. In other embodiments, core-shell capsules are fabricated without a membrane layer using a microfluidic or needle system to form microcapsules with two or more integrated layers. For example, two con-current liquid streams may be used to form two-layer droplets with the external stream containing the desired drug composition.

Cells suitable for encapsulation and transplantation are generally secretory or metabolic cells (i.e., they secrete a therapeutic factor or metabolize toxins, or both) or structural cells (e.g., skin, muscle, blood vessel), or metabolic cells (i.e., they metabolize toxic substances). In some embodiments, the cells are naturally secretory, such as islet cells that naturally secrete insulin, or naturally metabolic, such as hepatocytes that naturally detoxify and secrete. In some embodiments, the cells are bioengineered to express a recombinant protein, such as a secreted protein or metabolic enzyme. Depending on the cell type, the cells may be organized as single cells, cell aggregates, spheroids, or even natural or bioengineered tissue.

In some embodiments, the anti-inflammatory drugs are glucocorticoids, non-steroidal anti-inflammatory drugs (NSAIDs), phenolic antioxidants, anti-proliferative drugs, or combinations thereof. In some embodiments, the anti-inflammatory drug is lisofylline. Particularly preferred drugs include curcumin and dexamethasone.

An in vivo imaging system is used to identify anti-inflammatory drugs suitable for use in the disclosed compositions. The method involves monitoring the effect of candidate drugs loaded into polymeric particles on inflammatory enzymes and reactive oxygen species in the response against implanted biomaterials.

Methods for treating diseases generally involve administering to a subject a biocompatible hydrogel encapsulating mammalian cells and anti-inflammatory drugs. In some embodiments, the anti-inflammatory drugs are encapsulated in controlled release polymer. In some of these embodiments, the encapsulated cells preferably secrete a therapeutically effective amount of a substance to treat the disease for at least 30 days, preferably at least 60 days, more preferably at least 90 days. In particularly preferred embodiments, the cells are islet cells that secrete a therapeutically effective amount of insulin to treat diabetes in the subject for at least 30 days, preferably at least 60 days, more preferably at least 90 days.

BRIEF DESCRIPTION OF THE DRAWINGS

In FIG. 11A, the drug-loaded particles and cells are encapsulated together in the hydrogel. In FIG. 11B, the cells are encapsulated in a core hydrogel, and the drug-loaded particles are contained in an outer (envelope) hydrogel. An optional membrane material is shown separating the core and envelope hydrogels.

DETAILED DESCRIPTION OF THE INVENTION

I. Definitions

Figure 1:
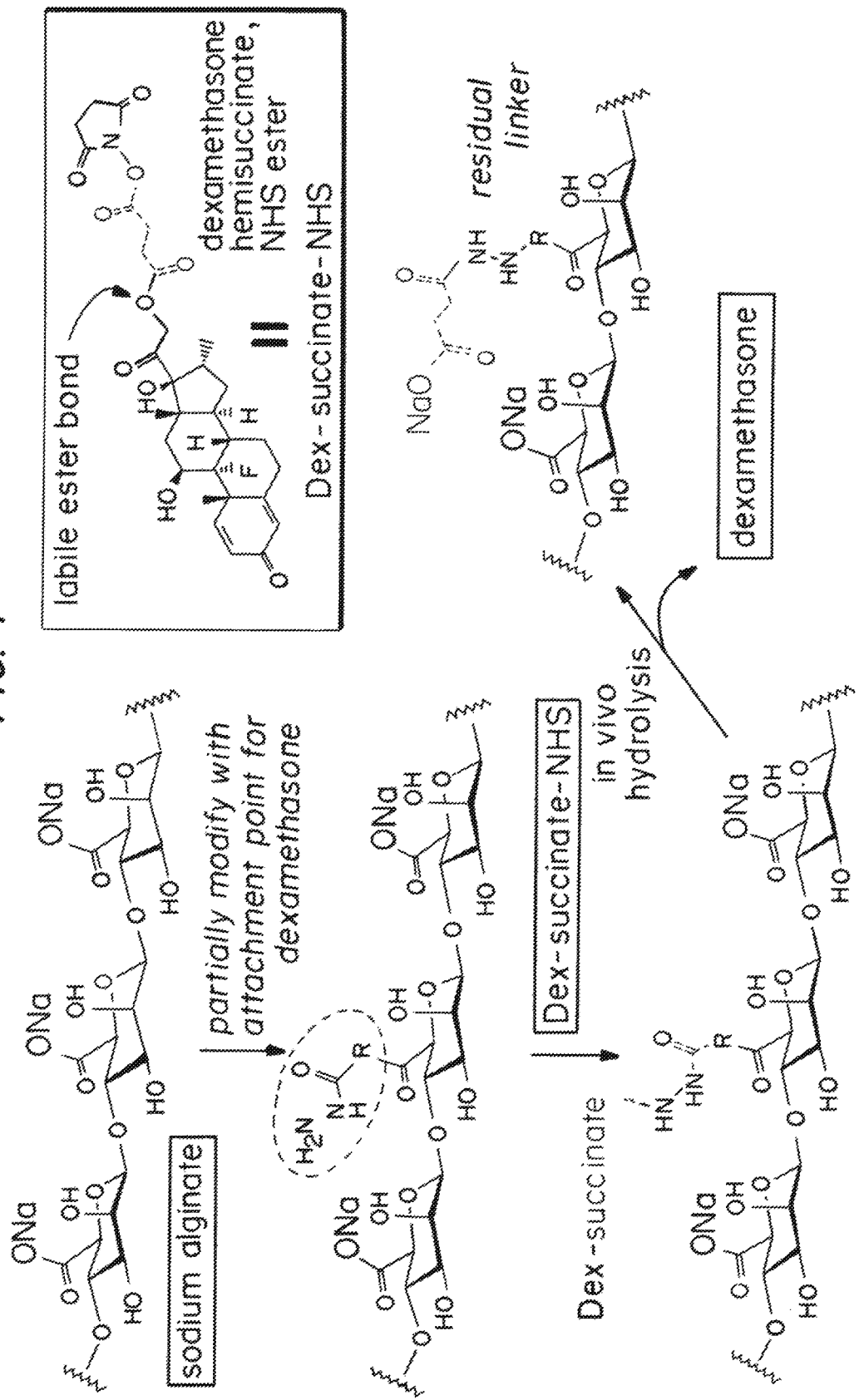
FIG. 1 illustrates the conjugation of dexamethasone to alginate to give extended low-dose release from alginate.

"Microcapsule" and "microgel" are used interchangeably to refer to a particle or capsule having a mean diameter of about 150 μm to about 1000 μm, formed of a cross-linked hydrogel or having a cross-linked hydrogel core that is surrounded by a polymeric shell. The microcapsule may have any shape suitable for cell encapsulation. The microcapsule may contain one or more cells dispersed in the cross-linked hydrogel, thereby "encapsulating" the cells.

"Hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer forms a gel which is not toxic to living cells, and allows sufficient diffusion of oxygen and nutrients to the entrapped cells to maintain viability.

"Alginate" is a collective term used to refer to linear polysaccharides formed from β-D-mannuronate and α-L-guluronate in any M/G ratio, as well as salts and derivatives thereof. The term "alginate", as used herein, encompasses any polymer having the structure shown below, as well as salts thereof.

nition. In some embodiments, the cell has been genetically engineered to express a recombinant protein and/or nucleic acid.

"Autologous" refers to a transplanted biological substance taken from the same individual.

"Allogeneic" refers to a transplanted biological substance taken from a different individual of the same species.

"Xenogeneic" refers to a transplanted biological substance taken from a different species.

"Islet cell" refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogenous populations of these cells. In preferred embodiments, a population of islet cells contains at least beta cells.

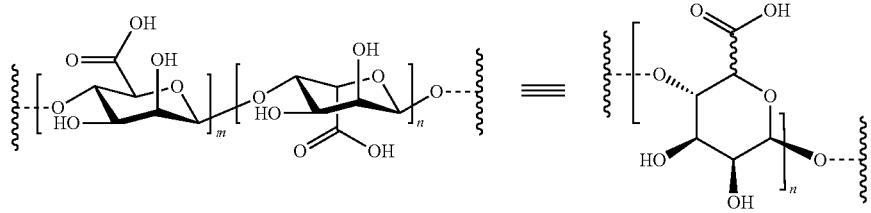

"Biocompatible" generally refers to a material and any metabolites or degradation products thereof that are generally non-toxic to the recipient and do not cause any significant adverse effects to the subject.

"Biodegradable" generally refers to a material that will degrade or erode by hydrolysis or enzymatic action under physiologic conditions to smaller units or chemical species that are capable of being metabolized, eliminated, or excreted by the subject. The degradation time is a function of polymer composition and morphology.

"Drug-loaded particle" refers to a polymeric particle having a drug dissolved, dispersed, entrapped, encapsulated, or attached thereto.

"Microparticle" and "nanoparticle" refer to a polymeric particle of microscopic and nanoscopic size, respectively, optionally containing a drug dissolved, dispersed, entrapped, encapsulated, or attached thereto.

"Anti-inflammatory drug" refers to a drug that directly or indirectly reduces inflammation in a tissue. The term includes, but is not limited to, drugs that are immunosuppressive. The term includes anti-proliferative immunosuppressive drugs, such as drugs that inhibit the proliferation of lymphocytes.

"Immunosuppressive drug" refers to a drug that inhibits or prevents an immune response to a foreign material in a subject. Immunosuppressive drug generally act by inhibiting T-cell activation, disrupting proliferation, or suppressing inflammation. A person who is undergoing immunosuppression is said to be immunocompromised.

"Mammalian cell" refers to any cell derived from a mammalian subject suitable for transplantation into the same or a different subject. The cell may be xenogeneic, autologous, or allogeneic. The cell can be a primary cell obtained directly from a mammalian subject. The cell may also be a cell derived from the culture and expansion of a cell obtained from a subject. For example, the cell may be a stem cell. Immortalized cells are also included within this defi- "Transplant" refers to the transfer of a cell, tissue, or organ to a subject from another source. The term is not limited to a particular mode of transfer. Encapsulated cells may be transplanted by any suitable method, such as by injection or surgical implantation.

II. Encapsulated Cells with Reduced Fibrosis

Compositions are disclosed for transplanting mammalian cells into a subject. The composition is formed from a biocompatible, hydrogel-forming polymer encapsulating the cells to be transplanted. In order to inhibit capsular overgrowth (fibrosis), the composition further contains one or more anti-inflammatory drugs dispersed in or on, and/or encapsulated in a biocompatible hydrogel. In a preferred embodiment, one or more anti-inflammatory drugs are present in drug-loaded polymeric particles for controlled release. In preferred embodiments, the hydrogel is an anionic polymer that is cross-linked with a polycationic polymer to form a shell.

Compartmentalizing the drug to the surface of the composition facilitates outward drug diffusion, maximizes drug interaction with immune cells, and minimizes interference with the mammalian cells inside. Therefore, in preferred embodiments the composition is configured with a core and envelope structure. In these embodiments, the mammalian cells are preferably encapsulated in the core hydrogel and the drug-loaded polymeric particles are encapsulated within the envelope hydrogel. In preferred embodiments, the core and envelope hydrogels are separated by a membrane or shell.

A. Biocompatible Polymers for Encapsulating Cells

The disclosed compositions are formed from a biocompatible, hydrogel-forming polymer encapsulating the cells to be transplanted. Examples of materials which can be used to form a suitable hydrogel include polysaccharides such as alginate, polyphosphazines, poly(acrylic acids), poly(methacrylic acids), poly(alkylene oxides), poly(vinyl acetate), polyvinylpyrrolidone (PVP), and copolymers and blends of each. See, for example, U.S. Pat. Nos. 5,709,854, 6,129,761 and 6,858,229.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups and sulfonic acid groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

The biocompatible, hydrogel-forming polymer is preferably a water-soluble gelling agent. In preferred embodiments, the water-soluble gelling agent is a polysaccharide gum, more preferably a polyanionic polymer.

The cells are preferably encapsulated using an anionic polymer such as alginate to provide the hydrogel layer (e.g., core), where the hydrogel layer is subsequently cross-linked with a polycationic polymer (e.g., an amino acid polymer such as polylysine) to form a shell. See e.g., U.S. Pat. Nos. 4,806,355, 4,689,293 and 4,673,566 to Goosen et al.; U.S. Pat. Nos. 4,409,331, 4,407,957, 4,391,909 and 4,352,883 to Lim et al.; U.S. Pat. Nos. 4,749,620 and 4,744,933 to Rha et al.; and U.S. Pat. No. 5,427,935 to Wang et al. Amino acid polymers that may be used to crosslink hydrogel forming polymers such as alginate include the cationic poly(amino acids) such as polylysine, polyarginine, polyornithine, and copolymers and blends thereof.

1. Polysaccharides

Several mammalian and non-mammalian polysaccharides have been explored for cell encapsulation. Exemplary polysaccharides suitable for cell encapsulation include alginate, chitosan, hyaluronan (HA), and chondroitin sulfate. Alginate and chitosan form crosslinked hydrogels under certain solution conditions, while HA and chondroitin sulfate are preferably modified to contain crosslinkable groups to form a hydrogel.

In preferred embodiments, the biocompatible, hydrogel-forming polymer encapsulating the cells is an alginate. Alginates are a family of unbranched anionic polysaccharides derived primarily from brown algae which occur extracellularly and intracellularly at approximately 20% to 40% of the dry weight. The 1,4-linked $\alpha$-1-guluronate (G) and $\beta$-d-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with l-fucose four-sulfate blocks as the major component. Commercial alginates are often extracted from algae washed ashore, and their properties depend on the harvesting and extraction processes.

Alginate forms a gel in the presence of divalent cations via ionic crosslinking. Although the properties of the hydrogel can be controlled to some degree through changes in the alginate precursor (molecular weight, composition, and macromer concentration), alginate does not degrade, but rather dissolves when the divalent cations are replaced by monovalent ions. In addition, alginate does not promote cell interactions.

A particularly preferred composition is a microcapsule containing cells immobilized in a core of alginate with a polylysine shell. Preferred microcapsules may also contain an additional external alginate layer (e.g., envelope) to form a multi-layer alginate/polylysine-alginate/alginate-cells microcapsule. See U.S. Pat. No. 4,391,909 to Lim et al. for description of alginate hydrogel crosslinked with polylysine. Other cationic polymers suitable for use as a cross-linker in place of polylysine include poly($\beta$-amino alcohols) (PBAAs) (Ma M, et al. Adv. Mater. 23:14189-94 (2011).

Chitosan is made by partially deacetylating chitin, a natural nonmammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times, but better cell adhesion due to increased hydrophobicity. Under dilute acid conditions (pH<6), chitosan is positively charged and water soluble, while at physiological pH, chitosan is neutral and hydrophobic, leading to the formation of a solid physically cross-linked hydrogel. The addition of polyol salts enables encapsulation of cells at neutral pH, where gelation becomes temperature dependent.

Chitosan has many amine and hydroxyl groups that can be modified. For example, chitosan has been modified by grafting methacrylic acid to create a crosslinkable macromer while also grafting lactic acid to enhance its water solubility at physiological pH. This crosslinked chitosan hydrogel degrades in the presence of lysozyme and chondrocytes. Photopolymerizable chitosan macromer can be synthesized by modifying chitosan with photoreactive azidobenzoic acid groups. Upon exposure to UV in the absence of any initiator, reactive nitrene groups are formed that react with each other or other amine groups on the chitosan to form an azo crosslink.

Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. Together, these qualities make HA attractive for tissue engineering scaffolds. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Auricular chondrocytes can be encapsulated in photopolymerized HA hydrogels where the gel structure is controlled by the macromer concentration and macromer molecular weight. In addition, photopolymerized HA and dextran hydrogels maintain long-term culture of undifferentiated human embryonic stem cells. HA hydrogels have also been fabricated through Michael-type addition reaction mechanisms where either acrylated HA is reacted with PEG-tetrathiol, or thiol-modified HA is reacted with PEG diacrylate.

Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups. The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydrogels of chondroitin sulfate and an inert polymer, such as PEG or PVA, may also be used.

2. Synthetic Polymers

Polyethylene glycol (PEG) has been the most widely used synthetic polymer to create macromers for cell encapsulation. A number of studies have used poly(ethylene glycol) di(meth)acrylate to encapsulate a variety of cells. Biodegradable PEG hydrogels can be been prepared from triblock copolymers of poly($\alpha$-hydroxy esters)-b-poly (ethylene glycol)-b-poly($\alpha$-hydroxy esters) endcapped with (meth)acrylate functional groups to enable crosslinking. PLA and poly(8-caprolactone) (PCL) have been the most commonly used poly($\alpha$-hydroxy esters) in creating biodegradable PEG macromers for cell encapsulation. The degradation profile and rate are controlled through the length of the degradable block and the chemistry. The ester bonds may also degrade by esterases present in serum, which accelerates degradation. Biodegradable PEG hydrogels can also be fabricated from precursors of PEG-bis-[2-acryloyloxy propanoate]. As an alternative to linear PEG macromers, PEG-based dendrimers of poly(glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

The biocompatible, hydrogel-forming polymer can contain polyphosphoesters or polyphosphates where the phosphoester linkage is susceptible to hydrolytic degradation resulting in the release of phosphate. For example, a phosphoester can be incorporated into the backbone of a crosslinkable PEG macromer, poly(ethylene glycol)-di-[ethylphosphatidyl (ethylene glycol) methacrylate] (PhosPEG-dMA), to form a biodegradable hydrogel. The addition of alkaline phosphatase, an ECM component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivitization of the polyphosphoester polymer.

Polyphosphazenes are polymers with backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R. groups are attached in this manner are known as polyaminophosphazenes). For polyimidazolephosphazenes, some of the "R" groups on the polyphosphazene backbone are imidazole rings, attached to phosphorous in the backbone through a ring nitrogen atom.

B. Conjugation of Drugs to Hydrogel-Forming Polymer

In some embodiments, one or more anti-inflammatory drugs are covalently attached to the hydrogel forming polymer. In these cases, the anti-inflammatory drug are attached to the hydrogel forming polymer via a linking moiety that is designed to be cleaved in vivo. The linking moiety can be designed to be cleaved hydrolytically, enzymatically, or combinations thereof, so as to provide for the sustained release of the anti-inflammatory drug in vivo. Both the composition of the linking moiety and its point of attachment to the anti-inflammatory agent, are selected so that cleavage of the linking moiety releases either an anti-inflammatory agent, or a suitable prodrug thereof. The composition of the linking moiety can also be selected in view of the desired release rate of the anti-inflammatory agents.

Linking moieties generally include one or more organic functional groups. Examples of suitable organic functional groups include secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROW), disulfide groups, hydrazones, hydrazides, ethers (—O—), and esters (—COO—, —CH$_2$O$_2$C—, CHRO$_2$C—), wherein R is an alkyl group, an aryl group, or a heterocyclic group. In general, the identity of the one or more organic functional groups within the linking moiety can be chosen in view of the desired release rate of the anti-inflammatory agents. In addition, the one or more organic functional groups can be chosen to facilitate the covalent attachment of the anti-inflammatory agents to the hydrogel forming polymer. In preferred embodiments, the linking moiety contains one or more ester linkages which can be cleaved by simple hydrolysis in vivo to release the anti-inflammatory agents.

In certain embodiments, the linking moiety includes one or more of the organic functional groups described above in combination with a spacer group. The spacer group can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms. Examples of suitable spacer groups include alkyl groups, heteroalkyl groups, alkylaryl groups, oligo- and polyethylene glycol chains, and oligo- and poly(amino acid) chains. Variation of the spacer group provides additional control over the release of the anti-inflammatory agents in vivo. In embodiments where the linking moiety includes a spacer group, one or more organic functional groups will generally be used to connect the spacer group to both the anti-inflammatory agent and the hydrogel forming polymer.

In certain embodiments, the one or more anti-inflammatory agents are covalently attached to the hydrogel forming polymer via a linking moiety which contains an alkyl group, an ester group, and a hydrazide group. By way of exemplification, FIG. 1 illustrates conjugation of the anti-inflammatory agent dexamethasone to alginate via a linking moiety containing an alkyl group, an ester group connecting the alkyl group to the anti-inflammatory agent, and a hydrazide group connecting the alkyl group to carboxylic acid groups located on the alginate. In this embodiment, hydrolysis of the ester group in vivo releases dexamethasone at a low dose over an extended period of time.

Reactions and strategies useful for the covalent attachment of anti-inflammatory agents to hydrogel forming polymers are known in the art. See, for example, March, "Advanced Organic Chemistry," 5$^{th}$ Edition, 2001, Wiley-Interscience Publication, New York) and Hermanson, "Bioconjugate Techniques," 1996, Elsevier Academic Press, U.S.A. Appropriate methods for the covalent attachment of a given anti-inflammatory agent can be selected in view of the linking moiety desired, as well as the structure of the anti-inflammatory agents and hydrogel forming polymers as a whole as it relates to compatibility of functional groups, protecting group strategies, and the presence of labile bonds.

C. Anti-Inflammatory and Anti-Proliferative Drugs

Drugs suitable for use in the disclosed compositions are described and can be identified using disclosed methods. Representative drugs include glucocorticoids, phenolic antioxidants, anti-proliferative drugs, or combinations thereof. These are collectively referred to herein as "anti-inflammatory drugs" unless stated otherwise.

Non-limiting examples include steroidal anti-inflammatories. Particularly preferred steroidal anti-inflammatory drugs include dexamethasone, 5-FU, daunomycin, and mitomycin. Anti-angiogenic or anti-proliferative drugs are also useful. Examples include curcumins including monoesters and tetrahydrocurcumin, and drugs such as sirolimus (rapamycin), ciclosporin, tacrolimus, doxorubicin, mycophenolic acid and paclitaxel and derivatives thereof. In some embodiments, the anti-inflammatory drug is an mTOR inhibitor (e.g., sirolimus and everolimus). A new antiproliferative drug is biolimus A9, a highly lipophilic, semisynthetic sirolimus analogue with an alkoxy-alkyl group replacing hydrogen at position 42-O. Lisofylline is a synthetic small molecule with anti-inflammatory properties. In some embodiments, the anti-inflammatory drug is a calcineurin inhibitors (e.g., cyclosporine, pimecrolimus and tacrolimus).

In some embodiments, the anti-inflammatory drug is a synthetic or natural anti-inflammatory protein. Antibodies specific to select immune components can be added to immunosuppressive therapy. In some embodiments, the anti-inflammatory drug is an anti-T cell antibody (e.g., anti-thymocyte globulin or Anti-lymphocyte globulin), anti-IL-2Rα receptor antibody (e.g., basiliximab or daclizumab), or anti-CD20 antibody (e.g., rituximab).

In preferred embodiments, the one or more anti-inflammatory drugs are released from the capsules after administration to a mammalian subject in an amount effective to inhibit fibrosis of the composition for at least 30 days, preferably at least 60 days, more preferably at least 90 days. In some embodiments, the anti-inflammatory drugs provide spatially localized inhibition of inflammation in the subject without systemic immunosuppression for at least 10 days, preferably at least 14 days, more preferably at least 30 days. In some embodiments, spatially localized inflammation is detected by measuring cathepsin activity at the injection sites in the subject. In other embodiments, spatially localized inflammation is detected by measuring reactive oxygen species (ROS) at the injection site in the subject. In some embodiments, systemic immunosuppression is detected by measuring no cathepsin activity or ROS at control sites in the subject, e.g., sites injected with drug-free polymeric particle or hydrogel. Methods for identifying, selecting, and optimizing anti-inflammatory drugs for use in the disclosed compositions are described below.

Figure 2:
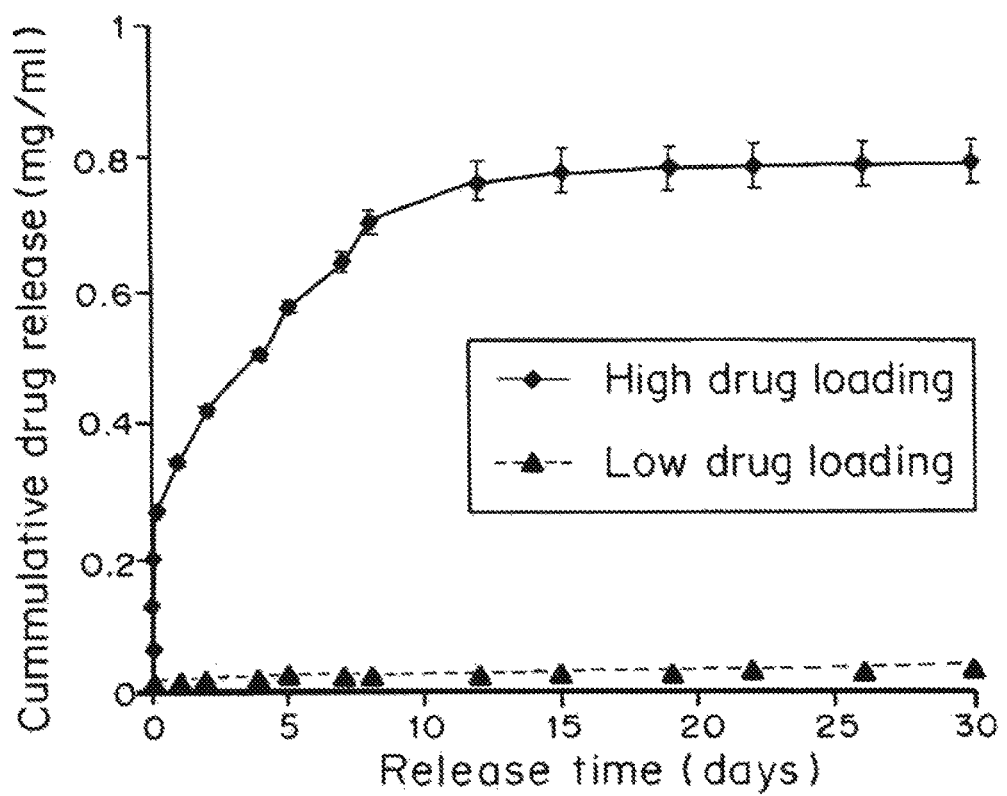
FIG. 2 is a graph showing drug release (mg/nil) profiles of dexamethasone from microparticles with high (-♦-, 26 wt %) and low (-▲-, 1.3 wt %) drug loading as a function of time (days).

The release rate and amounts can be selected in part by modifying drug loading of the polymeric particle. As disclosed herein, higher drug loading can cause a significant initial burst release (FIG. 2). This can also result in systemic immunosuppression rather than spatially localized inhibition of inflammation. In contrast, drug loading levels that are too low will not release therapeutically effective amounts of anti-inflammatory drug.

The optimal drug loading will necessarily depend on many factors, including the choice of drug, polymer, hydrogel, cell, and site of implantation. In some embodiments, the one or more anti-inflammatory drugs are loaded in the polymeric particle at a concentration of about 0.01% to about 15%, preferably about 0.1% to about 5%, more preferably about 1% to about 3% by weight. In some embodiments, the one or more anti-inflammatory drugs are encapsulated in the hydrogel at a concentration of 0.01 to 10.0 mg/ml of hydrogel, preferably 0.1 to 4.0 mg/ml of hydrogel, more preferably 0.3 to 2.0 mg/ml of hydrogel. However, optimal drug loading for any given drug, polymer, hydrogel, cell, and site of transplantation can be identified by routine methods, such as those described herein.

D. Biodegradable Polymers for Drug Delivery

The drug-loaded particles containing anti-inflammatory drugs are preferably formed from a biocompatible, biodegradable polymer suitable for drug delivery. In general, synthetic polymers are preferred, although natural polymers may be used and have equivalent or even better properties, especially some of the natural biopolymers which degrade by hydrolysis, such as some of the polyhydroxyalkanoates.

Representative synthetic polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), polyethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with PEG.

In the most preferred embodiment, PLGA is used as the biodegradable polymer. PLGA microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. For example, the hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

The diameter and porosity of the drug-loaded particle can be optimized based on the drug to be delivered and the desired dosage and rate of release. In preferred embodiments, the drug-loaded particle is a microparticle or a nanoparticle. The mean diameter of the particle may be selected and optimized based on the particular drug, dosage, and release rate needed. In preferred embodiments, the drug loaded polymeric particles are microparticles having a mean diameter of about 1 µm to about 100 µm, preferably about 1 µm to about 50 µm, more preferably about 1 µm to about 10 µm. In other embodiments, drug loaded polymeric particles are nanoparticles having a mean diameter of about 10 nm to about 999 nm, including at least about 50 nm, preferably at least about 100 nm, more preferably at least about 200 nm.

E. Microcapsules

The disclosed compositions are preferably microcapsules. The rate of molecules entering the capsule necessary for cell viability and the rate of therapeutic products and waste material exiting the capsule membrane are selected by modulating macrocapsule permeability. Macrocapsule permeability is also modified to limit entry of immune cells, antibodies, and cytokines into the microcapsule.

It has been shown that since different cell types have different metabolic requirements, the permeability of the membrane has to be optimized based on the cell type encapsulated in the hydrogel. The diameter of the microcapsules is an important factor that influences both the immune response towards the cell microcapsules as well as the mass transport across the capsule membrane. In some embodiments, the cell-loaded microcapsules has a mean diameter of about 150 µm to about 1000 µm, more preferably 300 µm to about 750 µm, even more preferably about 200 µm to about 500 µm for effective diffusion across the semi-permeable membrane.

F. Cells

The cell type chosen for encapsulation in the disclosed compositions depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. The disclosed anti-inflammatory drugs combat the immune response elicited by the presence of such cells. In the case of autologous cells, the anti-inflammatory drugs reduce the immune response provoked by the presence of the foreign hydrogel materials or due to the trauma of the transplant surgery. Cells can be obtained from biopsy or excision of the patient or a donor, cell culture, or cadavers.

In some embodiments, the cells secrete a therapeutically effective substance, such as a protein or nucleic acid. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid.

Examples of cells for encapsulation in the disclosed compositions include hepatocytes, islet cells, parathyroid cells, cells of intestinal origin, cells derived from the kidney, and other cells acting primarily to synthesize and secret, or to metabolize materials. A preferred cell type is a pancreatic islet cell. Genetically engineered cells are also suitable for encapsulation according to the disclosed methods. In some embodiments, the cells are engineered to secrete blood clotting factors, e.g., for hemophilia treatment, or to secrete growth hormones. In some embodiments, the cells are contained in natural or bioengineered tissue. For example, the cells for encapsulation are in some embodiments a bioartificial renal glomerulus. In some embodiments, the cells are suitable for transplantion into the central nervous system for treatment of neurodegenerative disease.

The amount and density of cells encapsulated in the disclosed compositions, such as microcapsules, will vary depending on the choice of cell, hydrogel, and site of implantation. In some embodiments, the single cells are present in the hydrogel at a concentration of $0.1 \times 10^6$ to $4 \times 10^6$ cells/ml, preferred $0.5 \times 10^6$ to $2 \times 10^6$ cells/ml. In other embodiments, the cells are present as cell aggregates. For example, islet cell aggregates (or whole islets) preferably contain about 1500-2000 cells for each aggregate of 150 µm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

1. Islet Cells

In preferred embodiments, the disclosed compositions contain islet cells producing insulin. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to microencapsulation, using any suitable method of culturing islet cells as is known in the art. See e.g., U.S. Pat. No. 5,821,121 to Brothers. Isolated cells may be cultured in a medium under conditions that helps to eliminate antigenic components.

2. Genetically Engineered Cells

In some embodiments, the disclosed compositions contain cells genetically engineered to produce a therapeutic protein or nucleic acid. In these embodiments, the cell can be a stem cell (e.g., pluripotent), a progenitor cell (e.g., multipotent or oligopotent), or a terminally differentiated cell (i.e., unipotent). The cell can be engineered to contain a nucleic acid encoding a therapeutic polynucleotide such miRNA or RNAi or a polynucleotide encoding a protein. The nucleic acid can be integrated into the cells genomic DNA for stable expression or can be in an expression vector (e.g., plasmid DNA). The therapeutic polynucleotide or protein can be selected based on the disease to be treated and the site of transplantation. In some embodiments, the therapeutic polynucleotide or protein is anti-neoplastic. In other embodiments, the therapeutic polynucleotide or protein is a hormone, growth factor, or enzyme.

III. Methods

A. Cell Encapsulation with Polysaccharide Hydrogel

Methods for encapsulating cells in hydrogels are known. In preferred embodiments, the hydrogel is a polysaccharide. For example, methods for encapsulating mammalian cells in an alginate polymer are well known and briefly described below. See, for example, U.S. Pat. No. 4,352,883 to Lim.

Alginate can be ionically cross-linked with divalent cations, in water, at room temperature, to form a hydrogel matrix. An aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N+$--\∧∧/--$+NR_3$ can also be used. Aqueous solutions of the salts of these cations are added to the polymers to form soft, highly swollen hydrogels and membranes. The higher the concentration of cation, or the higher the valence, the greater is the degree of cross-linking of the polymer. Concentrations from as low as 0.005 M have been demonstrated to cross-link the polymer. Higher concentrations are limited by the solubility of the salt.

The preferred anions for cross-linking of polymers containing basic side chains to form a hydrogel are divalent and trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In a preferred embodiment, alginate capsules are fabricated from solution of alginate containing suspended cells using the encapsulator (such as an Inotech encapsulator). In some embodiments, alginates are ionically crosslinked with a polyvalent cation, such as $Ca^{2+}$, $Ba^{2+}$, or $Sr^{2+}$. In particularly preferred embodiments, the alginate is crosslinked using $BaCl_2$. In some embodiments, the capsules are further purified after formation. In preferred embodiments, the capsules are washed with, for example, HEPES solution, Krebs solution, and/or RPMI-1640 medium.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell attachment and viability can be assessed using standard techniques, such as histology and fluorescent microscopy. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase, Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. By "physiologically acceptable salt" is meant a salt that is not unduly deleterious to the physiological responsiveness of the cells encapsulated in the microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 milliMolar up to about 20 or 100 millimolar, most preferably about 2 to 10 millimolar. The duration of the incubation step is not critical, and may be from about 1 or 10 minutes to about 1 or 2 hours, or more (e.g., over night). The temperature at which the incubation step is carried out is likewise not critical, and is typically from about 4 degrees Celsius up to about 37 degrees Celsius, with room temperature (about 21 degrees Celsius) preferred.

B. In Vivo Imaging System

To identify anti-inflammatory drug candidates for incorporation in the disclosed encapsulated cell compositions, an in vivo imaging system was developed to monitor the effect of candidate drugs in reducing the activity of inflammatory enzymes and reactive oxygen species in the response against implanted biomaterials.

In the disclosed high throughput in vivo assay, candidate drugs encapsulated in a biocompatible, biodegradable polymer suitable for drug delivery (see discussion of these polymers above) are injected in an array format on the back of a mammalian test subject to facilitate high-throughput screening. In preferred embodiments, the animal test subject is a rodent, such as a mouse.

After subcutaneous injection of the polymer particles, cathepsin activity at the point of injection of the drug-loaded particles may be compared to cathepsin activity at the point of injection of control particles (e.g., drug free and/or containing a control drug) to compare the anti-inflammatory effect of the candidate drug on the foreign body response to the implanted particles using in vivo fluorescence imaging. Cathepsin activity can be monitored using a fluorescence substrate that is activated by cathespin, such as Prosense680.

In addition, or in the alternative, reactive oxygen species (ROS) at the point of injection of the drug-loaded particles may be compared to ROS activity at the point of injection of control particles (e.g., drug free and/or containing a control drug) to compare the anti-inflammatory effect of the candidate drug on the foreign body response to the implanted particles using in vivo luminescent imaging. ROS activity can be monitored using a chemical substrate, such as luminol, that exhibits chemiluminescence in the presence of an oxidizing agent.

In preferred embodiments, the biocompatibility of the materials is assessed with in the first 14 days (preferably at days 3, 7, and 10) post injection using in vivo fluorescence imaging. In some embodiments, the fluorescence or luminescence intensity measured at the injection site of the candidate drug-loaded particles is compared with the fluorescence or luminescence intensity measured at the implantation site of a negative control (e.g., drug-free particle). In preferred embodiments, a decreased fluorescence or luminescence intensity at the implantation site of the candidate drug-loaded particle compared to the fluorescence or luminescence intensity measured at the implantation site of the control identifies an anti-inflammatory drug suitable for use in the disclosed compositions. In these embodiments, a decrease in fluorescence or luminescence correlates with an increase in anti-inflammatory potential.

C. Treatment of Diseases or Disorders

Encapsulated cells can be administered, e.g., injected or transplanted, into a patient in need thereof to treat a disease or disorder. In some embodiments, the disease or disorder is caused by or involves the malfunction hormone- or protein-secreting cells in a patient. In these embodiments, hormone- or protein-secreting cells are encapsulated and administered to the patient. For example, encapsulated islet cells can be administered to a patient with diabetes. In other embodiments, the cells are used to repair tissue in a subject. In these embodiments, the cells form structural tissues, such as skin, bone, cartilage, muscle, or blood vessels. In these embodiments, the cells are preferably stem cells or progenitor cells.

1. Diabetes

The potential of using a bioartificial pancreas for treatment of diabetes mellitus based on encapsulating islet cells within a semi permeable membrane is extensively being studied by scientists. Microencapsulation protects islet cells from immune rejection and allows the use of animal cells or genetically modified insulin-producing cells.

The Edmonton protocol involves implantation of human islets extracted from cadaveric donors and has shown improvements towards the treatment of type 1 diabetics who are prone to hypoglycemic unawareness. However, the two major hurdles faced in this technique are the limited availability of donor organs and the need for immunosuppressants to prevent an immune response in the patient's body.

Several studies have been dedicated towards the development of bioartificial pancreas involving the immobilization of islets cells inside polymeric capsules. The first attempt towards this aim was demonstrated in 1980 by Lim et al where xenograft islet cells were encapsulated inside alginate polylysine microcapsules, which resulted in significant in vivo results for several weeks.

The polymers typically used for islet microencapsulation are alginate, chitosan, polyethylene glycol (PEG), agarose, sodium cellulose sulfate and water insoluble polyacrylates.

2. Cancer

The use of cell encapsulated microcapsules towards the treatment of several forms of cancer has shown great potential. One approach undertaken by researchers is through the implantation of microcapsules containing genetically modified cytokine secreting cells. Genetically modified IL-2 cytokine secreting non-autologous mouse myoblasts implanted into mice delay tumor growth with an increased rate of survival of the animals. However, the efficiency of this treatment was brief due to an immune response towards the implanted microcapsules. Another approach to cancer suppression is through the use of angiogenesis inhibitors to prevent the release of growth factors that lead to the spread of tumors. Genetically modified cytochrome P450 expressing cells encapsulated in cellulose sulfate polymers may also be useful for the treatment of solid tumors.

3. Heart Diseases

While numerous methods have been studied for cell administration to enable cardiac tissue regeneration in patients after ischemic heart disease, the efficiency of the number of cells retained in the beating heart after implantation is still very low. A promising approach to overcome this problem is through the use of cell microencapsulation therapy which has shown to enable a higher cell retention as compared to the injection of free stem cells into the heart.

Another strategy to improve the impact of cell based encapsulation technique towards cardiac regenerative applications is through the use of genetically modified stem cells capable of secreting angiogenic factors such as vascular endothelial growth factor (VEGF), which stimulate neovascularization and restore perfusion in the damaged ischemic heart.

4. Liver Diseases

Microencapsulated hepatocytes can be used in a bioartificial liver assist device (BLAD). Acute liver failure (ALF) is a medical emergency which, despite improvements in modern intensive care, still carries a substantial mortality rate. In the most severe cases, urgent orthotopic liver transplantation (OLT) currently represents the only chance for survival. However, the supply of donor organs is limited and an organ may not become available in time. An effective temporary liver support system would improve the chance of survival in this circumstance by sustaining patients until a donor liver becomes available. Furthermore, the known capacity of the native liver to regenerate following recovery from ALF raises the possibility that the use of temporary liver support for a sufficient period of time may even obviate the need for OLT in at least some cases.

In some embodiments, hepatocytes are encapsulated in a microcapsules having of an inner core of modified collagen and an outer shell of terpolymer of methyl methacrylate (MMA), methacrylate (MAA) and hydroxyethyl methacrylate (HEMA) (Yin C, et al. Biomaterials 24:1771-1780 (2003)).

Cell lines which have been employed or are currently undergoing investigation for use in bioartificial liver support systems include primary hepatocytes isolated from human or animal livers, and various transformed human cells, such as hepatoma, hepatoblastoma and immortalised hepatocyte lines.

The present invention will be further understood by reference to the following non-limiting examples.

EXAMPLES

Example 1: Effect of Drug Loading on Controlled-Release Properties

Materials and Methods

Fabrication and Characterization of PLGA Microparticles:

Microparticles with or without dexamethasone were prepared using a single-emulsion method (Jain R A. *Biomaterials* 21(23):2475-90 (2000)) with biodegradable PLGA 50/50 (inherent viscosity of 0.95-1.20 dL/g) from Lactel (Pelham, Ala.). Typically, a 5 mL solution of PLGA and dexamethasone dissolved in dichloromethane, at concentrations of 40 mg/ml and 2 mg/ml respectively, was quickly added to a 25 mL solution of 1% (w/v) polyvinyl alcohol and homogenized for 60 sec at 5000 rpm (Silverson L4R, Silverson Machines Ltd., Cheshire, England). The resulting suspension was quickly decanted into 75 mL of deionized water and stirred for 30 sec prior to rotary evaporation (Buchi Rotavap, Buchi, Switzerland) for 3 min. The suspension was washed five times by centrifugation at 3000 rpm for 3 min. The particles were collected by filtration using 0.2 μm filter, flash-frozen in liquid nitrogen, and lyophilized to dryness. Particle size distribution and morphology were examined by Scanning Electron Microscopy (JSM-6060, Jeol Ltd., Peabody, Mass., USA). Fluorescence spectra of the PLGA polymer microparticles were collected by a Fluorolog-3 spectroflurometer (Horiba Yvon Jobin, Edison, N.J., USA). The dexamethasone loading of all microparticles was determined by dissolving 2 mg of microspheres in 1 mL of acetonitrile and comparing the resulting UV absorbance at 234 nm to a standard curve of known concentrations of dexamethasone in acetonitrile, In vitro drug release kinetics: The sample preparation and separation methods reported elsewhere were utilized to study the release of drug from microparticles (D'Souza S S, et al. *Pharma Res* 23(3):460-74 (2006)). Briefly, 3.5 mg of dexamethasone-loaded PLGA microparticles were suspended in 1 mL of 0.9% (w/v) NaCl solution in a 1.5 mL centrifuge tube. The centrifuge tube was incubated at 37° C. on a tilt-table (Ames Aliquot Mixer, Miles). At predetermined intervals, the tube was centrifuged at 12 krpm for 5 min using an Eppendorf 5424 microcentrifuge. The supernatant was collected and replaced with an equal volume of fresh 0.9% (w/v) aqueous NaCl solution. After a release period of thirty days, the suspension of remaining particles was completely dissolved in acetonitrile overnight. The concentration of dexamethasone in all collected samples was quantified using UV absorbance at 234 nm against a standard curve of known drug concentrations. The percentage of drug release at each time point was calculated by normalizing the cumulative amount of drug collected at each point with the total amount of drug initially encapsulated in the particles. The release kinetics reported for each particle formulation was obtained from the average of quadruplicate experiments.

Animal Care:

The animal protocol was approved by the local animal ethics committees at Massachusetts Institute of Technology (Committee on Animal Care) and Children's Hospital Boston (Institutional Animal Care and Use Committee) prior to initiation of the study. Male SKH-1E mice at the age of 8-12 weeks were obtained from Charles River Laboratories (Wilmington, Mass., USA). The mice were housed under standard conditions with a 12-hour light/dark cycle at the animal facilities of Massachusetts Institute of Technology, accredited by the American Association of Laboratory Animal Care. Both water and food were provided ad libitum.

Subcutaneous Injection of Polymeric Microparticles:

Before subcutaneous injection of microparticles, mice were kept under inhaled anesthesia using 1-4% isoflurane in oxygen at a flow rate of 2.5 L/min. Lyophilized microparticles with or without encapsulated drug were suspended in sterile 0.9% (w/v) phosphate buffered saline at a concentration of 50 mg/mL. A volume of 100 μL of this suspension was injected subcutaneously via a 23G needle at each of the six spots on the back of the mouse.

In Vivo Fluorescent Imaging of Whole Animal:

Mice were started on a non-fluorescent alfalfa-free diet (Harlan Teklad, Madison, Wis., USA) three days prior to subcutaneous injections of microparticles and maintained on this diet till the desired sacrifice time point for tissue harvesting. The imaging probe ProSense-680 (VisEn Medical, Woburn, Mass., USA), at a concentration of 2 nmol in 150 μl of sterile phosphate buffered saline was injected into the mice tail vein. After 24 hours, in vivo fluorescence imaging was performed with an IVIS-Spectrum measurement system (Xenogen, Hopkinton, Mass., USA). The animals were maintained under inhaled anesthesia using 1-4% isoflurane in oxygen at a flow rate of 2.5 L/min. For monitoring cathepsin activity, whole-animal near-infrared fluorescent images were captured at an excitation of 605 nm and emission of 720 nm and under optimized imaging configurations. A binning of 8×8 and a field of view of 13.1 cm were used for imaging. Exposure time and f/stop (the opening size of the aperture) were optimized for each acquired image. Background autofluorescence of PLGA particles was also imaged at an excitation of 465 nm and emission of 560 nm. Data were analyzed using the manufacturer's Living Image 3.1 software. All images are presented in fluorescence efficiency which is defined as the ratio of the collected fluorescent intensity normalized against an internal reference to account for the variations in the distribution of incident light intensity. Regions of interest (ROIs) were determined around the site of injection. ROI signal intensities were calculated in fluorescent efficiency.

Results

The inhibitory effect of microparticles was investigated with different loadings of an anti-inflammatory drug. Dexamethasone, a synthetic steroid, was selected for incorporation into PLGA microparticles because it is the most potent long-acting glucocorticoid that has been reported to decrease cellular recruitment to implanted biomaterials (Zhong Y, et al. *Brain Res* 1148:15-27 (2007); Hickey T, et al. *J Biomed Mater Res* 61(2):180-7 (2002); Bhardwaj U, et al. *J Diabetes Sci Technol* 1(1): 8-17 (2007); Ju Y M, et al. *J Biomed Mater Res* 93(1):200-10 (2010)) and to minimize fibrotic deposition on FDA-approved pace-maker leads (Singarayar S, et al. *PACE* 28(4):311-5 (2005)). PLGA particles with or without different drug loadings were fabricated by a water-in-oil emulsion method. Each formulation of drug-loaded particles was tested via subcutaneous injections at three alternating sites on the dorsal side of each mouse. Control particles without encapsulated drug were similarly administered at the three remaining sites on the same mouse. Each mouse was imaged 24 hours after intravenous administration of Prosense680, a near-infrared fluorescent probe to detect the activity of cathepsin enzymes, which are inflammatory proteases secreted by immune cells (Bratlie K M, et al. *PLoS One* 5(4): e10032 (2010); Tung C H, et al. *Cancer Res* 60(17):4953-8 (2000)).

For the mouse with low (1.3 wt %) loading particles, cathepsin activity of inflammatory cells was observed at three injection sites with control particles. This near-infrared fluorescent signal was absent for the drug-loaded particles at the remaining sites on the same mouse. The juxtaposition of cathepsin-absent sites next to cathepsin-active sites suggested that the anti-inflammatory effect was spatially localized at the injection sites of dexamethasone-loaded particles. Though the mechanism of action for dexamethasone is not completely understood, it is known to act via a variety of pathways (Rhen T, et al. *New Engl J Med* 353(16):1711-23 (2005)) resulting in the attenuation of inflammatory cell cascades when administered systemically (Tuckermann J P, et al. *J Clin Invest* 117(5):1381-90 (2007)). Ex vivo histology studies also reported that this drug decreases fibroblastic recruitment and collagen production at implant sites (Morais J M, et al. *AAPS J* 12(2):188-96 (2010)). The disclosed data showed in vivo for the first time that controlled-release formulations of dexamethasone (1.3 wt % drug loading) exhibited specific and localized inhibition of cathepsin activity in host response to subcutaneously implanted materials.

With the higher drug loading (26 wt %), there appeared to be a systemic immunosuppressant effect causing the disappearance of cathepsin signals from all six injection sites. This might be due to the significant initial burst release from the particles with higher drug loading, as illustrated by the in vitro drug release profile (FIG. 2). Several mice administered with particles of high drug loading died after 7-10 days. Conversely, mice receiving particles with low drug loading maintained healthy body conditions till sacrifice at 28 days. Understanding the effect of drug loading on the in vivo inhibitory properties is important in selecting drug delivery formulations for incorporation into medical devices. Choosing an appropriate anti-inflammatory drug release profile may minimize unwanted side effects of systemic circulation, while ensuring sufficient mitigation of the host response to achieve long-term device performance.

Example 2: Time-Evolution of Cathepsin Activity

The in vivo host response to implanted materials is a dynamic process that involves many different cell types and biological pathways. Neutrophils, monocytes and macrophages release cathepsins during the process of degranulation (Faurschou M, et al. *Microbes Infect* 5(14):1317-27 (2003); Lominadze G, et al. *Mol Cell Proteomics* 4(10):1503 (2005)). To kinetically monitor the effect of controlled-release dexamethasone on the activity of these immune cells, cathepsin activity was imaged in mice administered with dexamethasone-loaded particles (1.3 wt % drug loading). The particles were injected subcutaneously on day 0. The imaging probe was injected intravenously on days 2, 9, 16, and 27. The mice were imaged with IVIS system on days 3, 10, 17, and 28.

Cathepsin activity in response to control PLGA 50/50 particles was highest at days 3 and 10, and decreased significantly at later time points. However, for the microparticles containing dexamethasone, such cellular activity was suppressed at earlier time points and remained absent over the entire period of 28 days. Quantification of the time-evolution of this cathepsin activity is presented in FIG. 2 showing statistically significant differences between the two particle formulations at days 3 and 10. This temporal analysis suggests that monitoring of cathepsin activity is useful in detecting the anti-inflammatory effect of controlled-release therapeutics in the early phase of host response.

Example 3: Time-Evolution of Cellular Infiltration

Materials and Methods

Tissue Harvest and Histology Processing:

At the desired time points, mice were euthanized via $CO_2$ asphyxiation. The injected microparticles and 1 $cm^2$ area of full thickness dermal tissue surrounding the implant were excised, placed in histology cassettes and fixed in 10% formalin overnight. Following fixation, the tissues were dehydrated by transferring the cassettes to 70% ethanol solutions. The polymer particles with surrounding fixed tissues were embedded in paraffin and sectioned into samples of 5 µm thickness. These samples were stained with hematoxylin and eosin (H&E) for histological analysis.

Histology Analysis by Laser Scanning Cytometry:

The extent of cellular infiltration to injected polymer spots was determined by semi-quantitative imaging cytometry using the iCys Research Imaging Cytometer with iNovator software (CompuCyte, Cambridge, Mass., USA). A scanning protocol for quantification was configured with excitation by blue 488 nm laser and a virtual channel for hematoxylin detection. Low resolution tissue scans with the 20× objective were performed to capture preliminary images of all tissue sections in each slide. High resolution tissue scans were subsequently acquired using the 40× objective and step size of 0.5 µm. The threshold in the hematoxylin channel for detection of cell nuclei was optimized to selectively contour individual nuclei. Cross-sectional areas of the polymer spots excluding the dermal and skeletal tissues were defined. The nuclei number and nuclei area measurements were taken from within these regions. The extent of cellular infiltration into each polymer spot was calculated as the ratio of the total nuclei area to total polymer cross-sectional area.

Statistical Analysis:

The values of the fluorescent signals and the extent of cellular infiltration were averaged and expressed as the mean±standard error of the mean. Comparisons of values were performed by the Student's two-tailed two-sample t-test. P values less than 0.05 were considered significant.

Results

To understand how the temporal dynamics of in vivo cathepsin activity was related to time-dependent cellular infiltration between the implanted microparticles, standard histological analysis of excised tissues was also performed. Three mice were sacrificed at days 3, 10, 17 and 28. The excised polymer and surrounding tissues were fixed, processed histologically and stained with Hematoxylin and Eosin.

Qualitative evaluation of samples collected on days 3 and 10 revealed that the central portions of many polymer sections were detached during histology processing, while samples collected on days 17 and 27 remained intact. The non-homogenous properties of dermal tissue containing polymer particles rendered it fragile during histological processing steps such as microtome sectioning and exposure to various organic solvents. In the earlier phase of the foreign body response, cellular layers surrounding the implants might have been thinner and weaker; hence samples on days 3 and 10 were more prone to dissociation from the dermal tissue. In the later phase of days 17 and 27, wound healing might have already resolved (Anderson 0.1M, et al. *Semin Immunol* 20(2):86-100 (2008)) with the formation of strong fibrotic capsules containing the particles; and thus the samples became more resilient during histology processing.

Despite the lower quality of samples collected on days 3 and 10, neutrophils infiltrating the spaces between polymer particles and minimal collagen deposition were observed for both control and drug-loaded samples. At the later time points of days 17 and 27, extensive macrophage infiltration and collagen deposition were observed throughout the polymer sections of control samples, while drug-loaded samples were free of cellular infiltration.

Figure 3A:
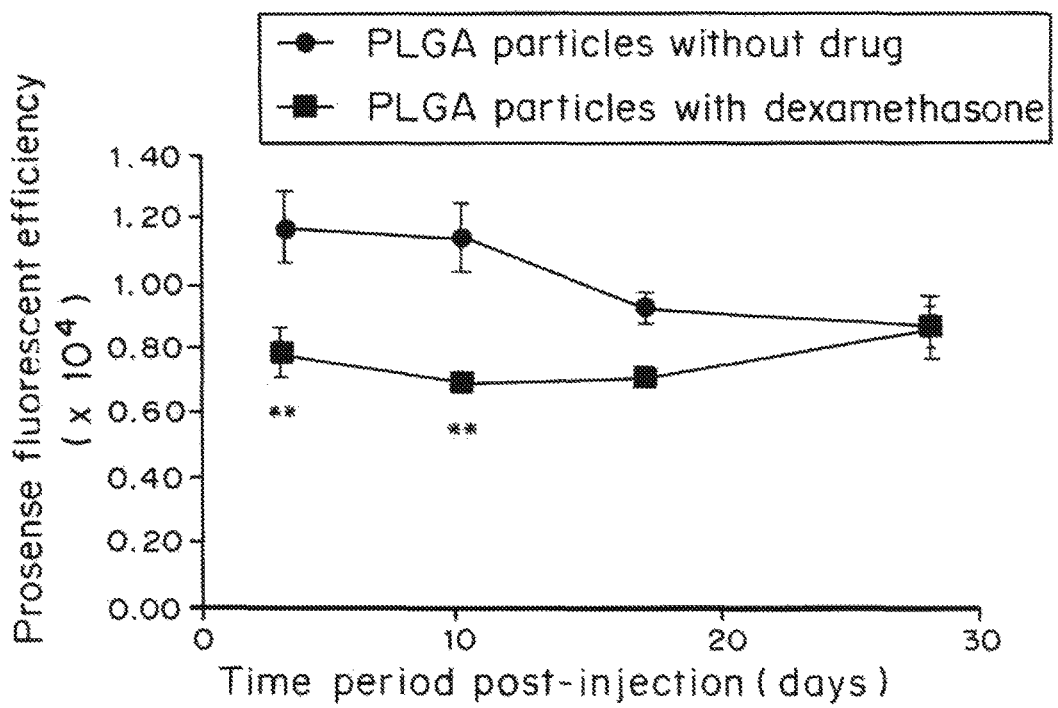
FIG. 3A is a graph showing near-infrared fluorescent efficiency (arbitrary units) 24 hours after intravenous administration of Prosense680, a near-infrared fluorescent probe used to detect the activity of cathepsin enzymes, in mice subcutaneously injected with PLGA microparticles containing 1.3 wt % dexamethasone (-■-) or no drug (-●-) as a function of time (days).
Figure 3B:
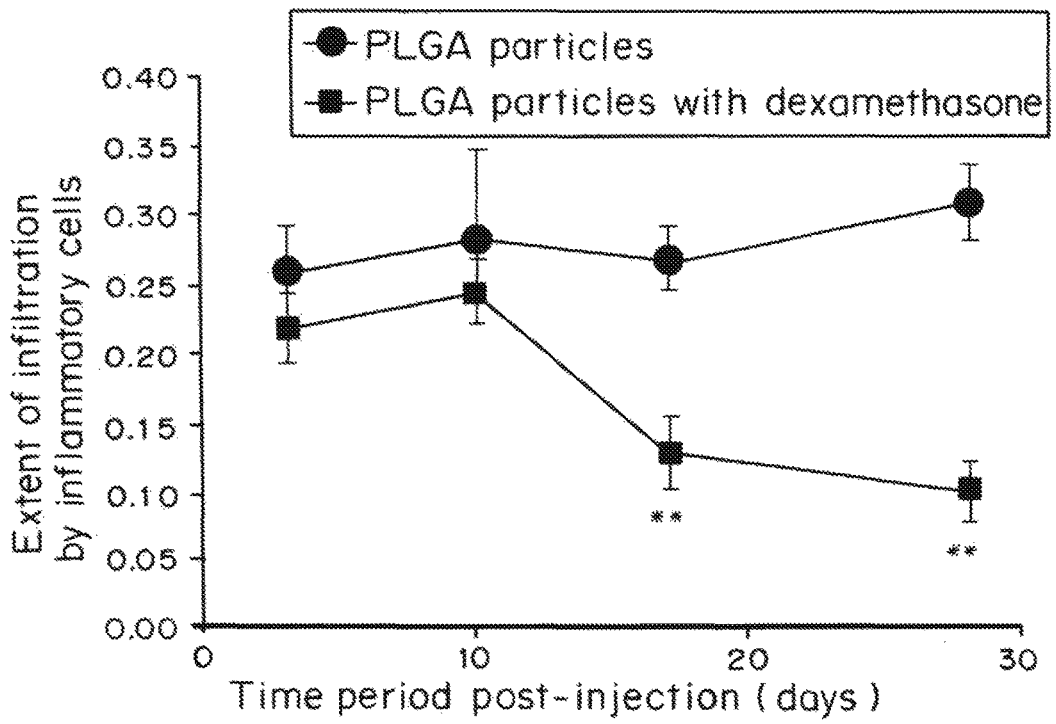
FIG. 3B is a graph showing cellular infiltration (ratio of total nuclei area to total polymer cross-sectional area) in mice subcutaneously injected with PLGA microparticles containing 1.3 wt % dexamethasone (-■-) or no drug (-●-) or as a function of time (days). ** $p<0.05$ by the Student's two-sample two-tailed t-test.

Laser scanning cytometry was used to quantify the amount of inflammatory cells recruited to the polymer injection sites according to established protocols (Hunt J A, et al. *J Mater Sci: Mater Med* 3(3):160-9 (1992); Zolnik B S, et al. *J Control Release* 127(2):137-45 (2008); Hunt J A, et al. *J Biomed Eng* 15(1):39-45 (1993); Hunt J A, et al. *Biomaterials* 16(3):167-70 (1995); Peterson R A, et al. *Toxicol pathol* 36(1):117 (2008)). FIG. 3B shows the extent of cellular infiltration into each polymer spot, calculated as the ratio of total nuclei area to total polymer cross-sectional area. The cellular coverage ratio was not statistically different for days 3 and 10, possibly due to the sample detachment at earlier time points. However, the extent of infiltration of inflammatory cells was significantly lower for drug-encapsulated polymers at later time points (days 17 and 27). Together, the histological data and fluorescent imaging provided complementary information to confirm that incorporation of dexamethasone decreased early protease activity and long-term cellular infiltration in the host response to subcutaneously implanted materials.

Example 4: Screening Anti-Inflammatory Drugs by an In Vivo Inflammation Imaging Assay Materials and Methods Fabrication and Characterization of PLGA Microparticles:

Microparticles with or without a drug were prepared using a single-emulsion method with biodegradable PLGA 50/50 (inherent viscosity of 0.95-1.20 dl/g) from Lactel (Pelham, Ala.). Typically, a 5 mL solution of PLGA dissolved in dichloromethane at concentrations of 40 mg/ml and a predetermined concentration of the desired drug, was quickly added to a 25 mL solution of 1% (w/v) polyvinyl alcohol and homogenized for 60 s at 5000 rpm (Silverson L4R, Silverson Machines Ltd., Cheshire, England). The resulting suspension was quickly decanted into 75 mL of deionized water and stirred for 30 s prior to rotary evaporation (Buchi Rotavap, Buchi, Switzerland) for 3 min. The suspension was washed five times by centrifugation at 3000 rpm for 3 min. The particles were collected by filtration using 0.2 μm filter, flash-frozen in liquid nitrogen, and lyophilized to dryness. Particle size distribution and morphology were examined by Scanning Electron Microscopy (JSM-6060, Jeol Ltd, Peabody, Mass., USA). The drug loading of all microparticles was determined by dissolving 2 mg of microspheres in 1 mL of acetonitrile and comparing the resulting UV absorbance (from UV-Vis spectrum or HPLC analysis) to a standard curve of known drug concentrations in acetonitrile.

Subcutaneous Injection of Polymers:

Before subcutaneous injection of the PLGA microparticles, mice were kept under inhaled anesthesia using 1-4% isoflurane in oxygen at a flow rate of 2.5 L/min. Lyophilized microparticles with or without encapsulated drug were suspended in sterile 0.9% (w/v) phosphate buffered saline at a concentration of 50 mg/mL. A volume of 100 μL of this suspension was injected subcutaneously via a 23G needle at each of the six spots on the back of each hairless immune competent SKH-1E mouse.

Non-Invasive Fluorescent and Bioluminescent Imaging:

Mice were started on a non-fluorescent alfalfa-free diet (Harlan Teklad, Madison, Wis., USA) three days prior to subcutaneous injections of microparticles and maintained on this diet till the desired sacrifice time point for tissue harvesting. To monitor cathepsin activity, the imaging probe ProSense-680 (VisEn Medical, Woburn, Mass., USA), at a concentration of 2 nmol in 150 ml of sterile phosphate buffered saline was injected into the mice tail vein. After 24 h, in vivo fluorescence imaging was performed with an IVIS-Spectrum measurement system (Xenogen, Hopkinton, Mass., USA). The animals were maintained under inhaled anesthesia using 1-4% isoflurane in oxygen at a flow rate of 2.5 L/min. Whole-animal near-infrared fluorescent images were captured at an excitation of 605 nm and emission of 720 nm and under optimized imaging configurations. To monitor reactive oxygen species, a volume of 200 ul of Sodium Luminol (Sigma Aldrich) dissolved in PBS buffer at a concentration of 50 mg/ml was injected intraperitoneally to each mouse prior to imaging (dose of 500 mg/kg). Ten minute after this injection, the mouse was imaged under bioluminescent setting in the IVIS system. Data were analyzed using the manufacturer's Living Image 3.1 software. Fluorescent images are presented in fluorescence efficiency which is defined as the ratio of the collected fluorescent intensity normalized against an internal reference to account for the variations in the distribution of incident light intensity. Regions of interest (ROIs) were determined around the site of injection. ROI signal intensities were calculated in total fluorescent efficiency for fluorescence images and in photons per second for bioluminescent images.

Tissue Retrieval and Histology Processing:

At the desired time points, mice were euthanized via $CO_2$ asphyxiation. The injected polymer and one square centimeter area of full thickness dermal tissue surrounding the implant were excised, placed in histology cassettes and fixed in 10% formalin overnight. Following fixation, the tissues were dehydrated by transferring the cassettes to 70% ethanol solutions. The polymer particles with surrounding fixed tissues were embedded in paraffin and sectioned into samples of 5 mm thickness. These samples were stained with hematoxylin and eosin (H&E) for histological analysis.

Animal Care and Use:

The animal protocol was approved by the local animal ethics committees at Massachusetts Institute of Technology (Committee on Animal Care) prior to initiation of the study.

Results

Hybrid alginate microcapsule designs were developed that contain anti-inflammatory drug selected from the screening of different classes of anti-inflammatory drugs by an in vivo inflammation imaging assay.

To identify promising anti-inflammatory drug candidate, an in vivo imaging system was used to monitor the effect of these drugs in reducing the activity of inflammatory enzymes and reactive oxygen species in the response against implanted biomaterials. PLGA microspheres containing small molecule anti-inflammatory drugs were subcutaneously injected at multiple sites on the back of hairless immune competent mice. Non-invasive fluorescent imaging of cathepsin activity by an activable probe, Prosense680 and luminescent imaging of reactive oxygen species with luminol were used to monitor the activity of immune cells in the early inflammatory phase while histology was used to provide information on long-term biocompatibility.

Seventeen different drugs were investigated, including non-steroidal and steroidal anti-inflammatory drugs as well as non-steroidal immunosuppressants. Each drug was encapsulated in PLGA microparticles at three different theoretical loading levels of 5%, 10% and 15% giving a total of 51 controlled release formulations. Preliminary in vivo screening of these formulations revealed that several formulations were able to inhibit cellular infiltration into the subcutaneous space between the injected microspheres. For example, in the first 10 days post-injection, PLGA microparticles incorporating the steroidal drug dexamethasone were able to locally suppress the cathepsin activity of inflammatory cells while the injection sites with control PLGA particles actively retain this enzymatic activity. This decrease in early inflammatory activity led to decreased cellular recruitment in later time points.

Other drug candidates for reducing the early inflammatory response to implanted biomaterials are listed Table 1.

TABLE 1

Different classes of drugs investigated with the in vivo inflammation imaging assay

| Drug name | Classification |
| --- | --- |
| dexamethasone | Steroidal |
| methylprednisolone | Steroidal |
| prednisolone | Steroidal |
| hydrocortisone | Steroidal |
| fludrocortisone | Steroidal |
| prednisone | Steroidal |
| rapamycin | Inhibitor of response to IL-2 |

TABLE 1-continued

Different classes of drugs investigated with the in vivo inflammation imaging assay

| Drug name | Classification |
| --- | --- |
| cyclosporin | Blocker of production of IL-2 |
| tacrolimus/FK-506 | Blocker of production of IL-2 |
| paclitaxel | Interfere with microtube breakdown |
| curcumin | Naturally derived polyphenolic anti-oxidant |
| Resveratrol | Naturally derived polyphenolic anti-oxidant |
| celecoxib | Inhibitor of COX-2 enzymes |
| ketorolac | Inhibitor of COX-1 enzymes |
| piroxicam | Inhibitor of COX-1 enzymes |
| diclorofenac | Inhibitor of COX-1 enzymes |
| ibuprofen | Inhibitor of COX-1 enzymes |
| ketoprofen | Inhibitor of COX-1 enzymes |

Example 5: In Vitro Assessment of Drug Effects in a Co-Culture of Macrophages and Encapsulated Islets Materials and Methods In Vitro Characterization of Viability and Insulin Secretion Function of Encapsulated Islets:

RAW 264.7 macrophages were cultured in RPMI-1640 medium supplemented with 10% FBS, 100 units/ml penicillin and 100 µg/ml streptomycin (Invitrogen). The cells were sub-cultured every 2-3 days. 0.2 million macrophages in 3 ml of fresh culture medium were seeded into each well of a six-well tissue-culture treated polystyrene plate and allowed to adhere to the plate surface over night. The culture medium was removed and encapsulated islets were added in 3 ml of fresh medium to each well with adherent macrophages. Co-culturing of encapsulated islets with macrophages was maintained for four days. Afterwards, supernatant samples were collected and frozen at −20° C. for future insulin analysis with an insulin ELISA kit (ALPCO diagnostics). Encapsulated islets were collected into new plates. Both encapsulated islets and remaining adherent macrophages were washed in HEPES buffer and subjected to live-dead fluorescent staining (Invitrogen) for viability assessment.

Results

An in vitro experiment was designed to test whether the presence of immune cells affects insulin secretion by islets. Hybrid alginate capsules containing islet cells and 2 mg/ml of dexamethasone or 1 mg/ml of curcumin were fabricated. Islet cells were encapsulated alone as a positive control. As a negative control, encapsulated islets were co-cultured with a macrophage cell line adherent to the plate's bottom. To assess the effect of the co-encapsulated drugs, hybrid capsules containing islets and drug were co-cultured with the adherent macrophages which simulate the immune cells recruited to the surgical site during wound healing in the immediate post-transplant period. The encapsulated cells were cultured for 4 days, media samples were collected for insulin analysis, and islets were stained with live/dead dyes for viability assessment.

Figure 5:
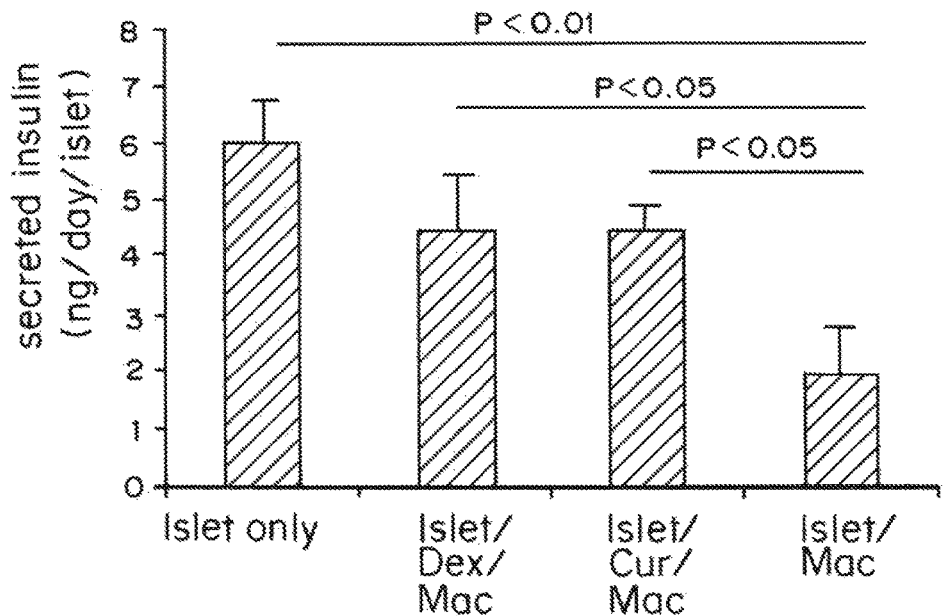
FIG. 5 is a graph showing insulin secretion (ng/day/islet) from islet cells encapsulated with no drug (columns 1 and 4), dexamethasone (column 2), or curcumin (column 3) and co-cultured with nothing (column 1) or with a macrophage cell line adherent to plate's bottom (columns 2-4).

Islets remained viable in the presence of dexamethasone or curcumin. Macrophages reduced insulin secretion from the encapsulated islet cells (FIG. 5). Therefore, immune cells can lower insulin concentration without attachment on capsules. Dexamethasone and curcumin hindered macrophages proliferation and restored insulin secretion (FIG. 5). These data suggests that locally released anti-inflammatory drugs in the immediate period post-transplant might help to minimize the recruitment of immune cells during the early phase of the wound healing process and hence mitigate the harmful effects of these cells on the insulin-secreting functions of encapsulated islets.

Example 6: Improved Efficacy of Hybrid Alginate Capsules Containing Islets and Anti-Inflammatory Drug in STZ-Induced Diabetic Mice Materials and Methods Fabrication of Hybrid Drug-Islet Encapsulated in Alginate Capsules:

Alginate with high gluronic acid content SLG20 (Novamatrix, FMC Polymer, Drammen, Norway) was dissolved in sterile 0.9% (w/v) NaCl to give an alginate solution of 1.5% (w/v). To prepare hybrid drug-islet capsule, 1.5% (w/v) alginate was mixed with curcumin (Sigma Aldrich) at 0.3-1.0 mg/ml or with dexamethasone (Sigma Aldrich) at 1-2 mg/ml and stirred for 3-4 days to ensure that the drug is homogenously dispersed. During this mixing period, curcumin-alginate mixture was wrapped in aluminium foil to avoid light exposure which might oxidize this drug. One day after islet isolation, islets were washed twice with Ca-free Krebs and mixed with the alginate suspension with or without dispersed drug at a pre-cross-linking islet density of approximately 750-1000 islets/ml. Islet-containing microcapsules were produced using an electrostatic droplet generator (6 kV) by extrusion of the islet-alginate suspension through a 22G needle at a volume flow rate of 0.155 ml/min into a cross-linking bath of 20 mM $BaCl_2$ solution. Encapsulated islets were then left to cross-link in this solution for another 5 minutes before being collected into a 50 ml Falcon tube. The capsules were subsequently washed four times with HEPES buffer and two times with RPMI-1640 medium supplemented with 10% FBS and 100 units/ml penicillin and 100 µg/ml streptomycin (Invitrogen). The final microcapsule diameter was in the range of 400-500

Animal Care and Use:

The animal protocol was approved by the local animal ethics committees at Massachusetts Institute of Technology (Committee on Animal Care) prior to initiation of the study. Male Sprague-Dawley rats, 200-250 g, also obtained from Charles River Laboratories, were used as islet donors. Diabetic male C57B6/J mice (Jackson Laboratory, Me., USA) were recipients of encapsulated islets. Diabetes was induced in C57B6/J mice via a research contract with Jackson Laboratory, Me., USA. Briefly, male C57B6/J mice, aged 6-8 weeks, were subjected to multiple low-dose intraperitoneal injections of streptozotocin (Sigma Aldrich) at a daily dose of 50 mg/kg. 200 µl of STZ freshly dissolved in Phosphate Buffered Saline at a concentration of 5 mg/ml was administered to each mouse daily for a period of 5 consecutive days. Injected mice were housed in disposable cages with appropriate absorbent bedding with food and water ad libitum. The mice were observed daily till after the final STZ injection when they are weighed and their blood glucose levels determined. Mice were confirmed diabetic if their non-fasted blood glucose level rose above 300 mg/dL for two consecutive daily readings. These mice were shipped to Massachusetts Institute of Technology and only those with stable hyperglycemia were used for subsequent transplantation. Mice were housed under standard conditions with a 12-hour light/dark cycle at the animal facilities of Massachusetts Institute of Technology, accredited by the American Association of Laboratory Animal Care. Both water and food were provided ad libitum. Prior to intraperitoneal glucose tolerance test (IPGTT), mice were fasted over night.

Transplantation of Rat Encapsulated Islets into STZ-Induced Diabetic Mice:

Xenogeneic transplants of encapsulated rat islets to diabetic mice recipients were performed to examine the reversibility of diabetes. One day after isolation from Sprague-Dawley rats, islets were encapsulated with or without an anti-inflammatory drug (curcumin or dexamethasone). Shortly thereafter, islet-containing capsules were sampled in quadruplicate, the total islets number was counted. Aliquots of the capsules suspended in culture media were prepared to contain an equal number of islets by collecting all of the capsules, dividing the number of capsules by volume of medium and carefully pipetting up and down to ensure capsules remained suspended while preparing aliquots. They were then transplanted intraperitoneally via a lapratomy procedure into diabetic C57B6/J mice under 1-4% isofluorane-in-oxygen anaesthesia through a 5-10 mm abdominal incision.

Daily Blood Glucose Monitoring:

Animal blood glucose was determined between 9:00-11:00 a.m. using a portable glucometer (Clarity Plus). Blood was taken from a tail vein with the total volume drawn per collection not exceeding 5 µl.

Intraperitoneal Glucose Tolerance Test (IPGTT):

Mice were fasted overnight (6:00 p.m.-9:00 a.m.) the night before IPGTT. On the day of the glucose challenge, each animal was injected intraperitoneally with 400 µl of 10% (w/v) of glucose in sterile 0.9% NaCl, and its blood glucose was taken at 15, 30, 60, 75, 90, 105 and 120 minutes post-injection. Diabetic and non-diabetic animals were also included as controls.

Results

Figure 6:
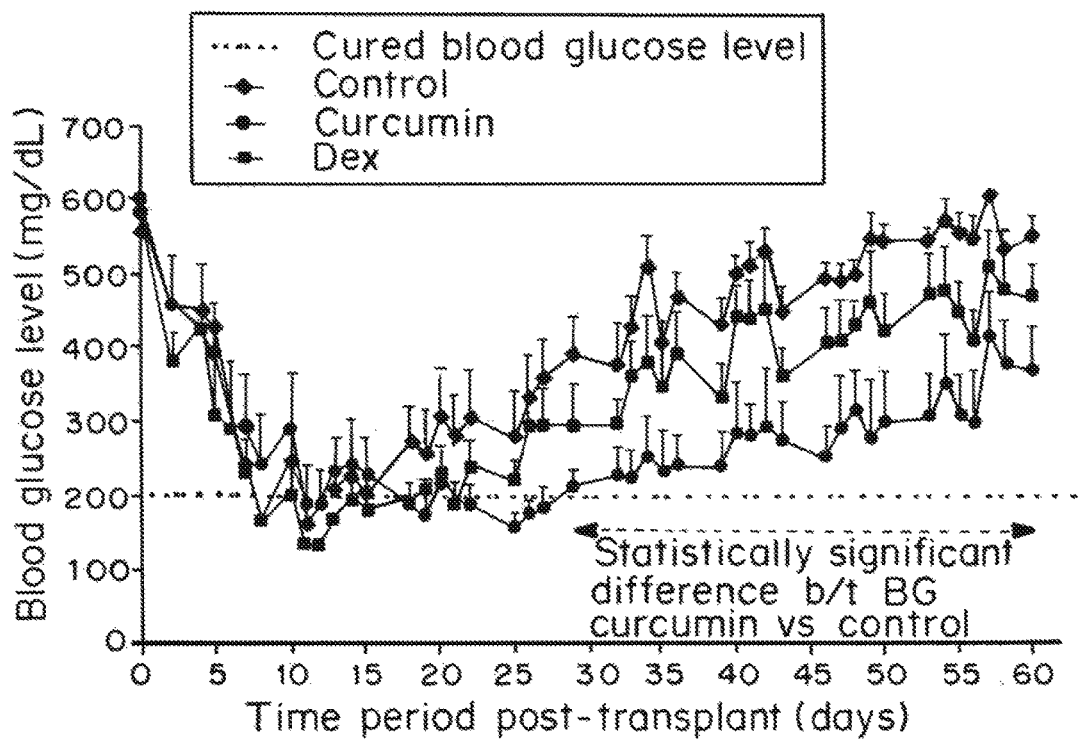
FIG. 6 is a graph showing blood glucose level (mg/dL) as a function of time (days post-transplantation) in C57/B6 mice with STZ-induced diabetes transplanted with islet cells encapsulated with no drug (-♦-), curcumin (-●-), or dexamethasone (-■-).
Figure 7:
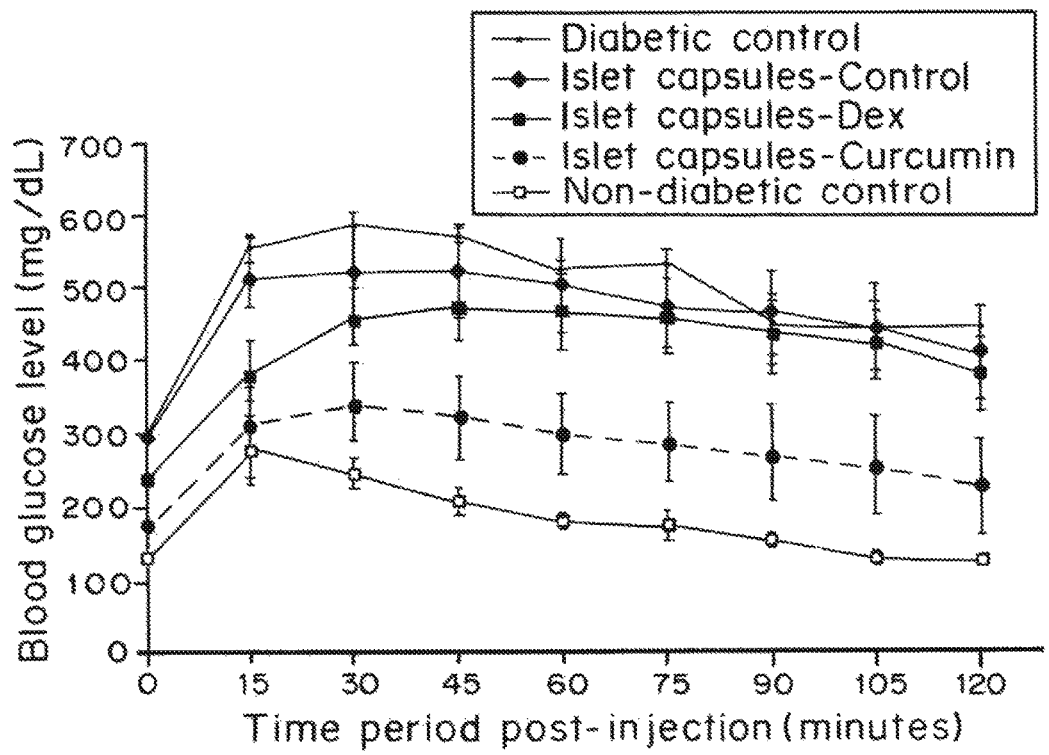
FIG. 7 is a graph showing blood glucose level (mg/dL) as a function of time (minutes) after intraperitoneal glucose challenge in non-diabetic control mice (-□-), diabetic control mice (---), or diabetic mice transplanted with islet cells encapsulated with no drug (-♦-), curcumin (-●-), or dexamethasone (-■-).

In order to assess the efficacy of hybrid alginate capsules containing islet cells and anti-inflammatory drug, C57/B6 mice with streptozotocin (STZ)-induced diabetes were transplanted with a marginal mass of alginate-encapsulated islets containing curcumin, dexamethasone or no drug (control) (n=6-7 replicate for each formulation). After the transplant surgery, all mice recovered well and maintained stable weight and body condition. These mice were monitored to record daily blood glucose over the period of 2 months. Both curcumin and dexamethasone improved glycemic control. Curcumin/islet capsules gave the best glycemic control with a prolonged average graft survival of about 30 days compared to about 20 days and 15 days by dexamethasone/islet capsules and control capsules respectively (FIG. 6). In the intraperitoneal glucose challenge test, curcumin/islet capsules also gave the best glucose clearance (FIG. 7)

Example 7: Quantitative Assessment of Fibrosis Formation on Retrieved Capsules by DNA Fluorescent Staining Materials and Methods Retrieval of Transplanted Capsule from the Intraperitoneal Cavity:

Sixty days after transplantation of islet-containing capsules, the mice from example 6 were sacrificed by $CO_2$ asphyxiation. A lapratomy was performed to expose the abdominal cavity and capsules were retrieved by an abdominal lavage with HEPES buffer. The abdominal cavity was examined closely to identify remaining capsules, which if found were gently removed using atraumatic tweezers. The retrieved capsules were subsequently washed several times in HEPES buffer and imaged at 2× magnification using an EVOS brightfield microscope (AMG). Finally, capsules were transferred into a 1.5 ml Eppendorf tube, and frozen at −20° C. for future analysis.

Quantification of Fibrosis by DNA Fluorescent Staining:

50 μl of retrieved capsules (120-150 alginate capsules) were transferred to each well of a 24-well Millicell® cell culture insert (Millipore) using wide-orifice pipette tips (Fisher Scientific, Pittsburgh, Pa., USA). The capsules were incubated at 37° C. for 45 min in 800 μl of 0.001 mg/ml Hoersch 33342 dye (Invitrogen) prepared from stock solution by dilution with HEPES buffer. Afterwards, these capsules were washed four times with HEPES buffer. The capsules were contained in the upper insert which had a porous bottom membrane separating the capsules from the lower container well. The use of a porous insert helped to avoid the loss of capsules during washing steps as washing buffer could be removed by aspiration from the lower well or draining away from the upper insert by placing a Kimwipe below the porous membrane. All capsules were subsequently transferred in 300 μl of HEPES buffer into a black 96 well plate (Greiner BioOne). Finally, fluorescent signals from the stained capsules were obtained using a Tecan UV-VIS absorbance plate reader at with the excitation and emission wavelengths of 350 nm and 460 nm respectively.

Results

Capsules retrieved from the mice in Example 6 were examined for fibrosis. Qualitative observation suggested that curcumin/islet capsules had the least fibrosis, whereas dexamethasone/islets capsules had as much fibrosis as the control capsules. The curcumin/islet capsules still retain a yellowish color of this drug indicating the presence of residual curcumin in the capsules.

Figure 8:
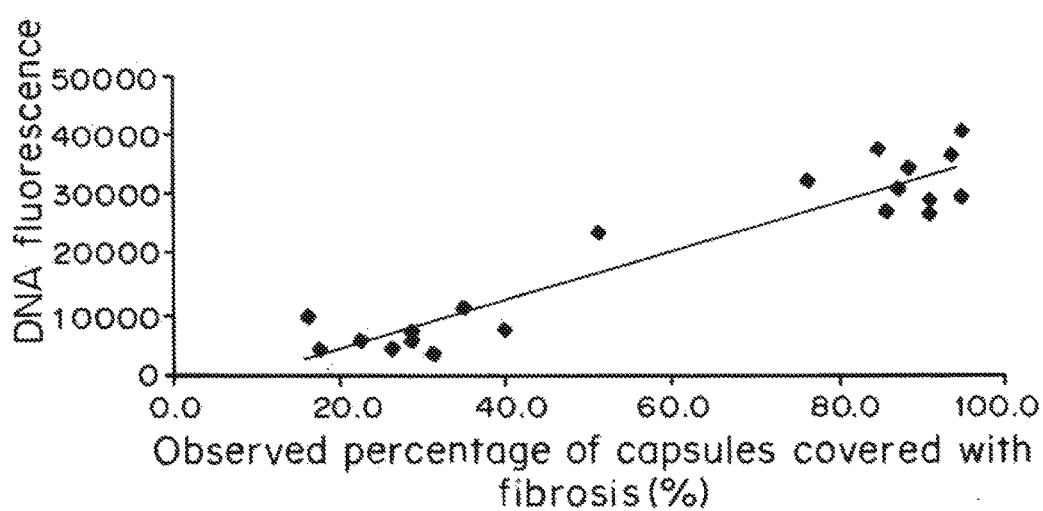
FIG. 8 is a plot showing DNA fluorescence (arbitrary units) of retrieved capsules as a function of the observed percentage of capsules covered with fibrosis (%). y=395x−3553; $R^2=0.888$.

A rigorous quantification technique was developed to assess fibrosis on capsules via DNA fluorescent staining. Capsules were stained with Hoersch dye which binds to DNA. The graph in FIG. 8 shows the DNA signal of 20 different samples plotted against the conventional scores. A good correlation (R2=0.888) was observed between DNA staining and average conventional score from 5 independent blinded individuals. These data establish that DNA staining can be used for fibrosis quantification.

Figure 9:
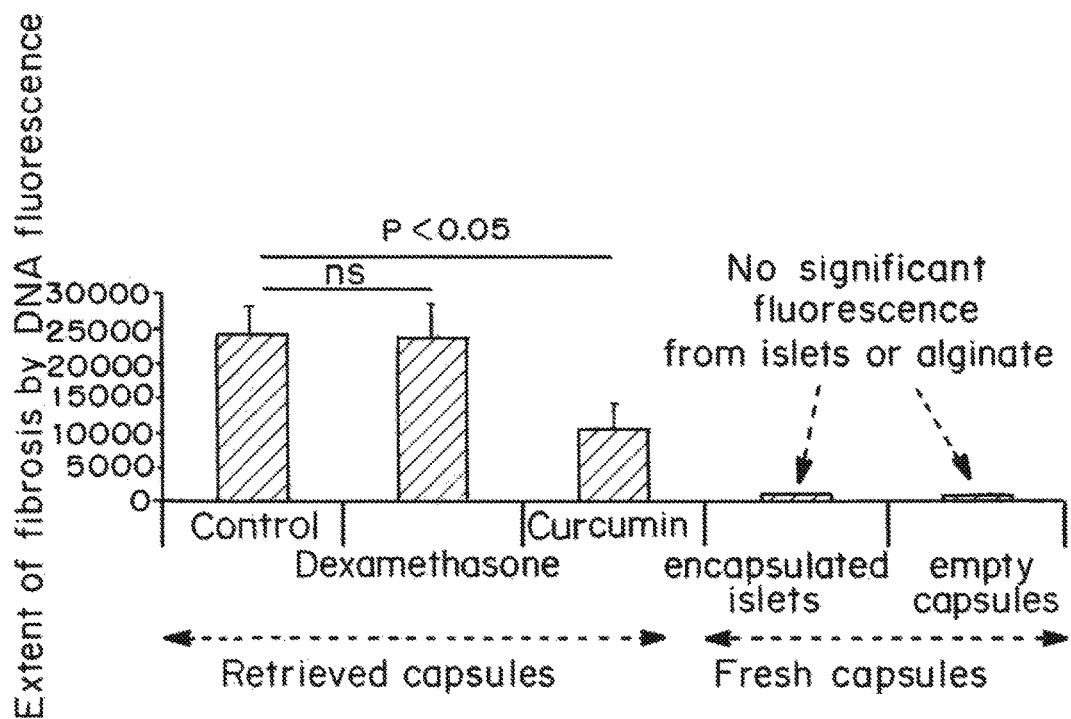
FIG. 9 is a bar graph showing DNA fluorescence (arbitrary units) of retrieved capsules (columns 1-3) containing islet cells and no drug (column 1), dexamethasone (column 2) or curcumin (column 3) or fresh capsules containing islet cells (column 4) or no cells (column 5).

Samples retrieved from the diabetic mice in Example 6 were stained for DNA fluorescence. Curcumin reduced fibrosis with statistical significance while dexamethasone did not (FIG. 9). The presence of islets did not contribute significantly to DNA signal (FIG. 9).

Figure 10:
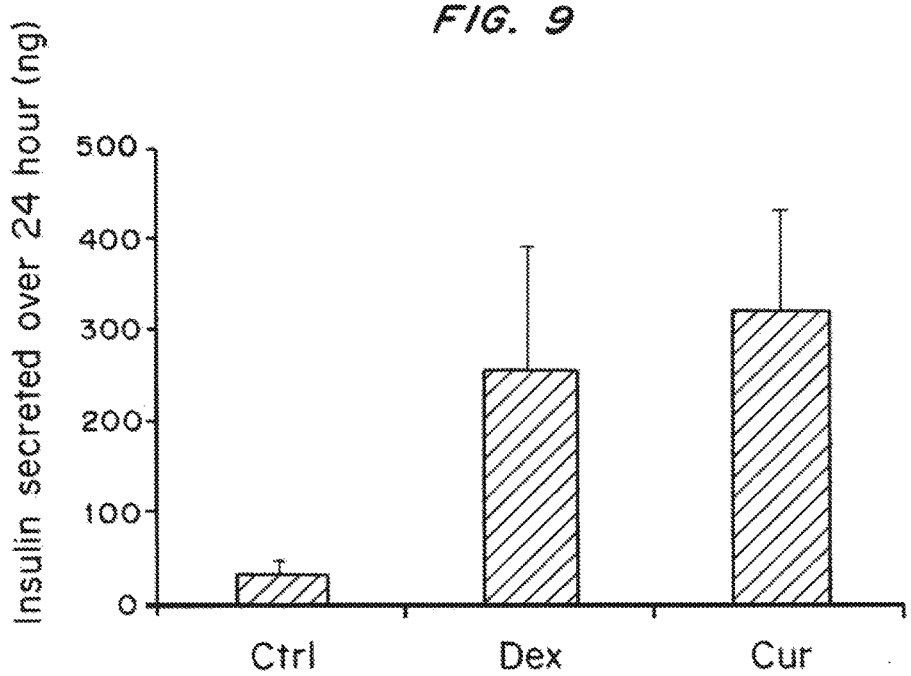
FIG. 10 is a bar graph showing insulin secretion (ng) over 24 hours from retrieved capsules containing islet cells and no drug (column 1), dexamethasone (column 2) or curcumin (column 3).

Insulin secretion was measured from the retrieved capsules for 24 hours. As shown in FIG. 10, both dexamethasone and curcumin greatly improved insulin secretion from the capsules.

Figure 11A:
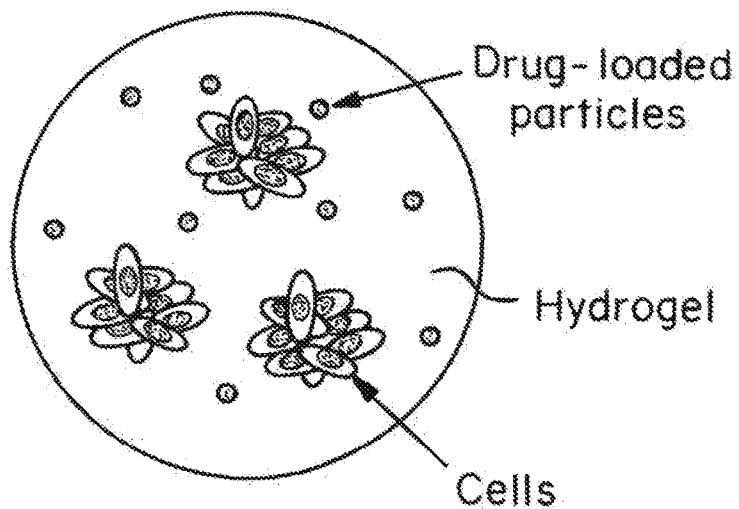
FIGS. 11A and 11B are illustrations of hydrogel microcapsules embodiments.
Figure 11B:
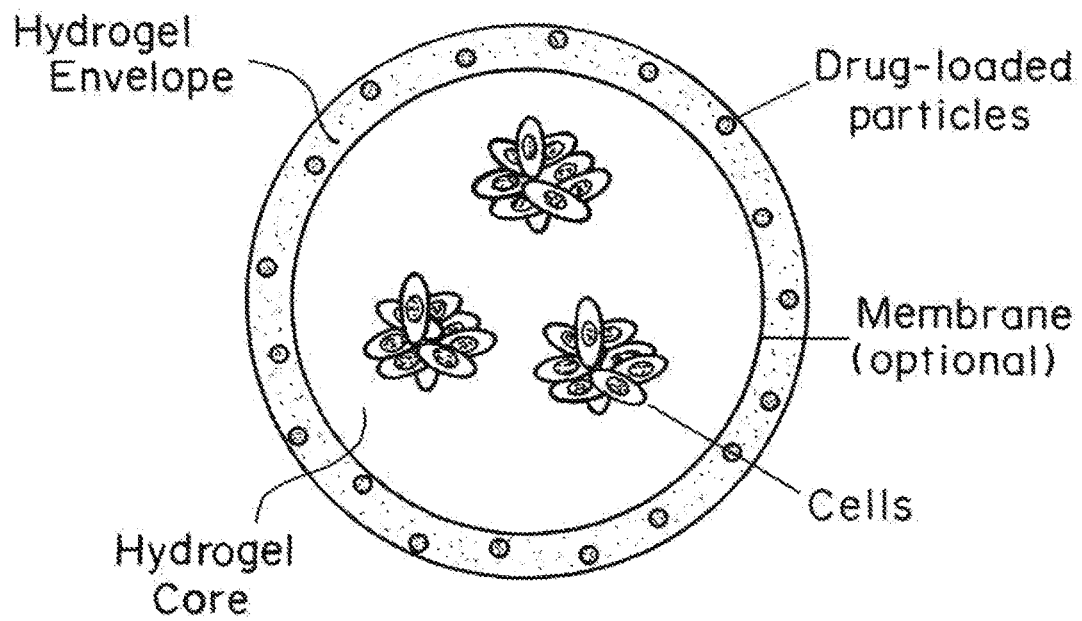
Figure 11C:
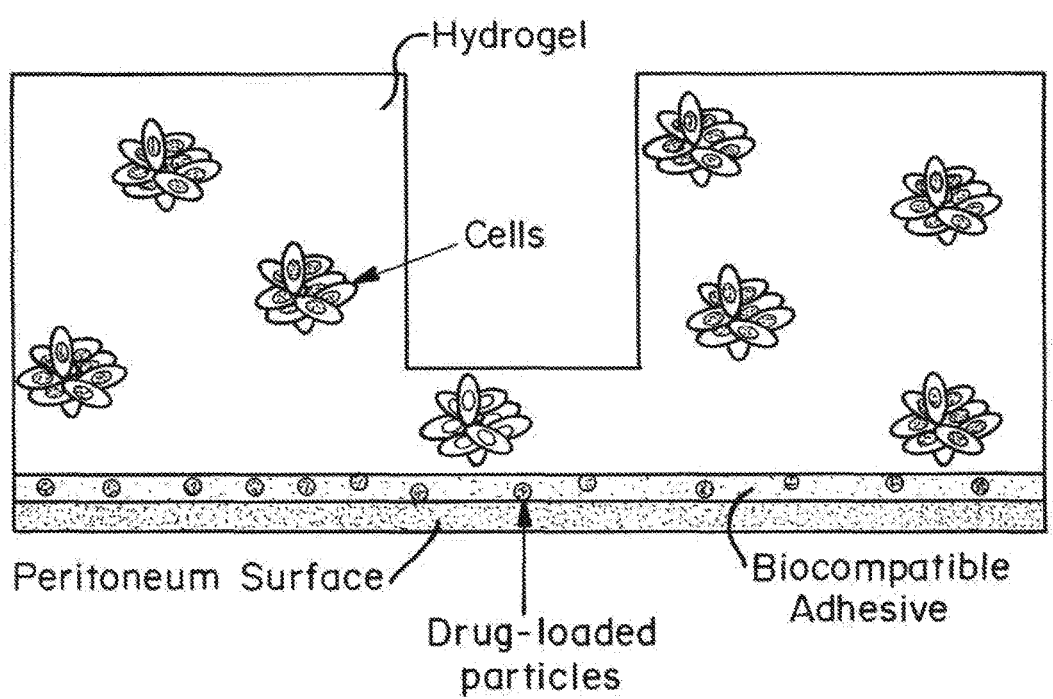
FIG. 11C is an illustration of a macrodevice embodiment formed by adhering hydrogel microcapsules to peritoneum using a biocompatible adhesive containing drug-loaded particles.

Example 8: Improved Efficacy of Hybrid Alginate Capsules Containing Islets and Anti-Inflammatory Drug in STZ-Induced Diabetic Mice Immuno-Stimulated with Lipopolysaccharide Materials and Methods Fabrication of Hybrid Drug-Islet Encapsulated in Alginate Capsules:

To incorporate candidate drugs into the alginate microcapsule system, two types of hybrid microcapsules containing islets and drug were designed (see FIGS. 11A-11B). Spherical alginate capsules were generated by a cell encapsulator using SLG 100 alginate at 2-2.5 wt % and cross-linked in a 20 mM $BaCl_2$ bath. For the first type of capsule, free anti-inflammatory drug or drug-loaded PLGA microspheres (1-10 μm) was mixed with the alginate and homogeneously dispersed in the alginate solution by overnight mixing (see FIG. 11).

For the second type of microcapsules, the drug-free alginate capsule was coated first with a layer of poly-L-lysine (0.01 wt %, 70-100 kDa) and then with 0.5 wt % alginate containing free drug or drug-loaded PLGA microspheres to form a thin external layer on the surface of the alginate capsules in a core-shell structure (sec FIG. 11B). Compartmentalizing the drug to the surface of the capsules facilitate outward drug diffusion to the peritoneal space and maximize drug interaction with immune cells while minimizing any interference with the islet inside.

Transplantation of Encapsulated Rat Islets into STZ-Induced Diabetic Mice with or without Lipopolysaccharide (LPS):

In order to assess hybrid alginate capsules containing islet cells and dexamethasone, C57/B6 mice with streptozotocin (STZ)-induced diabetes were transplanted via a lapratomy procedure with the first type of alginate-encapsulated islets containing dexamethasone or no drug (control). For the mice to be stimulated with LPS, each mice were intraperitoneally injected with one dose of 100 μl of LPS dissolved in PBS (1 mg/ml) on day 4 post-surgery. Daily blood glucose level was also monitored for these mice.

Results

Studies have suggested that non-specific immune activation caused by surgical trauma of implantation can cause early functional impairment and loss of cell mass of islet encapsulated in alginate (Cole, D R, et al. *Diabetologia* 35(3):231-237 (1992); de Vos, P, et al, *J Biomed Mater Res* 62(3):430-437 (2002); Robitaille, R, et al. *Biomaterials* 26(19):4119-4127 (2005)). This surgical injury induces an immunological cascade which is associated with secretion of cytotoxic cytokines, further recruitment of inflammatory cells and eventual fibrotic growth of a portion of the capsules. This problem is particularly severe and cause graft failure in higher animal models such as non-human primates which have a more aggressive immune systems.

Incorporation of anti-inflammatory drugs has been proposed to inhibit this early inflammatory response and improve the biocompatibility of alginate capsules (Blasi, P, et al. *Int J Pharm* 324(1):27-36 (2006); Bünger, C. M, et al. *Biomaterials* 26(15):2353-2360 (2005); Ricci, M, et al. *J Control Release* 107(3):395-407 (2005)). However, the pool of explored anti-inflammatory drugs is small and, no encapsulation strategy has shown the efficacy these drugs in improving islet performance in diabetic treatment. The disclosed inflammation imaging method allows one to systematically screen several classes of anti-inflammatory drugs, identify promising drug candidates, and incorporate them into engineered alginate capsules containing islets for transplantation into diabetic animal models. These hybrid capsules were able to improve the glycemic control of immune-isolated islets transplanted in diabetic mice.

Figure 4A:
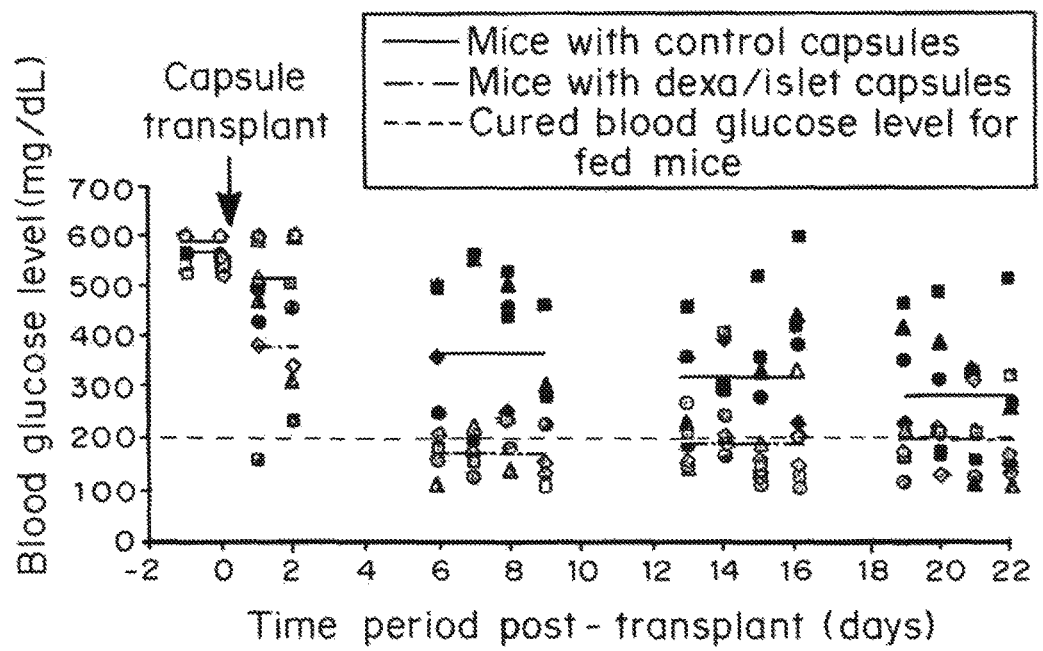
FIG. 4A is a plot showing blood glucose levels (mg/dL) in streptozotocin (STZ)-induced C57/B6J diabetic mice (N=5 per group) transplanted with microcapsules containing rat islets with (shaded shapes) and without (solid shapes) dexamethasone as a function of time post-transplantation (days).

To illustrate the efficacy of drug-embedded capsule design in diabetes treatment, two groups of capsules containing rat islets with and without embedded dexamethasone were transplanted into two sets of STZ-induced C57/B6J diabetic mice without LPS stimulation (n=5 per group), and their efficacy in curing diabetes was followed by daily monitoring of blood glucose level. FIG. 4A shows the blood glucose level of these diabetic mice up to 22 days. The group of mice with drug-embedded islet capsules showed a faster decrease in blood glucose level and a tighter glycemic control during these 22 day period. All mice with drug-embedded capsules were cured (blood glucose below 200 mg/dL) while mice with control capsules remained hyperglycemic. This data indicates that administration of locally released anti-inflammatory drug from the capsules can improve the performance of islet grafts in the immediate time period after transplant surgery.

Figure 4B:
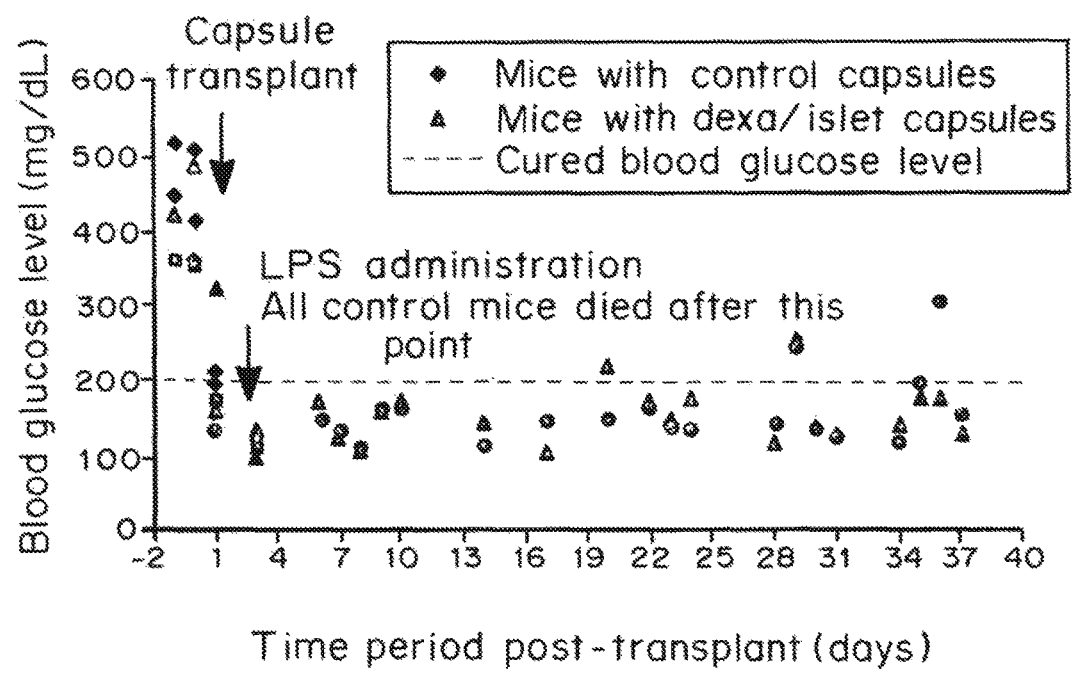
FIG. 4B is a plot showing blood glucose levels (mg/dL) in STZ-induced C57/B6J diabetic mice (N=3 per group) transplanted with microcapsules containing rat islets with (shaded shapes) and without (solid shapes) dexamethasone and subjected to 1 dose of Lipo-Polysaccharide (LPS) immunostimulation challenge as a function of time post-transplantation (days). Control mice did not survive LPS challenge.

To illustrate the same efficacy in a mouse model with a more aggressive immune system, two groups of diabetic mice (n=3) transplanted with control and hybrid dexamethasone/islet capsules were subjected to 1 dose of LPS stimulation. LPS is a component of bacterial cell wall which can stimulate the immune system of mice giving rise to more aggressive recruitment of inflammatory cells. With LPS priming, mice with drug-embedded capsules demonstrate rapid and sustained correction of blood glucose level up to 37 days (FIG. 4B). In contrast, mice with control capsules did not survive the aggressive immuno-stimulation. This data indicates that administration of controlled release anti-inflammatory drug can improve islet performance in more aggressive inflammation model.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising:
   (a) (i) a core comprising a biocompatible hydrogel and encapsulating one or more allogeneic or autologous mammalian secretory, metabolic or structural cells, (ii) an envelope on the outside of the core comprising a biocompatible hydrogel, and (iii) optionally a membrane separating the core and the envelope; and
   (b) one or more anti-inflammatory drugs encapsulated in or on polymeric particles dispersed on or within the core, the envelope or within the envelope and the core;
   wherein the one or more anti-inflammatory drugs are locally released from the composition after implantation in a mammalian subject in an amount effective to prevent detectable fibrosis of the composition for at least 10 days.

2. The composition of claim 1, comprising a membrane separating the core and the envelope.

3. The composition of claim 2, wherein the membrane comprises polycation crosslinked hydrogel.

4. The composition of claim 1, wherein the composition is a microcapsule or a coating on or within an implantable device.

5. The composition of claim 1, wherein the composition is in the form of microcapsules, having a mean diameter of between about 150 μm and about 1000 μm, between about 300 μm and about 750 μm, between about 200 μm and about 500 μm, or between about 400 μm and about 500 μm.

6. The composition of claim 1, comprising polymeric microparticles, having a mean diameter of between about 1 μm and about 100 μm, between about 1 μm and about 50 μm, between about 1 μm and about 10 μm, between about 10 nm and about 999 nm, between about 50 nm and 500 nm, or about 100 nm.

7. The composition of claim 1, wherein the biocompatible hydrogel in the core or the envelope comprises a polymer selected from the group consisting of a polysaccharide, polyphosphazene, poly(acrylic acids), poly(methacrylic acids), copolymers of acrylic acid and methacrylic acid, poly(alkylene oxides), poly(vinyl acetate), polyvinylpyrrolidone (PVP), and copolymers and blends thereof.

8. The composition of claim 7, wherein the biocompatible hydrogel in the core comprises a polysaccharide selected from the group consisting of alginate, chitosan, hyaluronan, and chondroitin sulfate.

9. The composition of claim 7, wherein the biocompatible hydrogel in the envelope comprises a polysaccharide selected from the group consisting of alginate, chitosan, hyaluronan, and chondroitin sulfate.

10. The composition of claim 1, wherein the one or more mammalian secretory, metabolic or structural cells are allogeneic.

11. The composition of claim 1, wherein the one or more mammalian secretory cells are islet cells.

12. The composition of claim 1, wherein the one or more mammalian secretory, metabolic or structural cells are genetically engineered.

13. The composition of claim 1, wherein the one or more anti-inflammatory drugs is selected from the group consisting of glucocorticoids, phenolic antioxidants, and anti-proliferative drugs.

14. The composition of claim 13, wherein the one or more anti-inflammatory drugs are drugs that directly or indirectly reduce inflammation in a tissue or anti-proliferative immunosuppressive drugs that inhibit the proliferation of lymphocytes.

15. The composition of claim 1, wherein the one or more anti-inflammatory drugs inhibit fibrosis of the composition after transplantation in the subject by at least 50% compared to the same composition not including anti-inflammatory drug.

16. The composition of claim 1, wherein the one or more anti-inflammatory drugs are released from the composition after implantation in an amount effective to provide spatially localized inhibition of cathepsin activity without systemic immunosuppression.

17. The composition of claim 1, wherein the one or more anti-inflammatory drugs are conjugated to the biocompatible hydrogel in the envelope by a biodegradable chemical linker.

18. A method for treating or alleviating one or more symptoms of a disease in a subject, comprising administering to a subject in need thereof an effective amount of a composition of claim 1.

19. A method for identifying and selecting suitable anti-inflammatory drugs to prevent fibrosis of encapsulated cells, comprising:
   (a) providing a microparticle formed from a biocompatible, biodegradable polymer comprising a candidate anti-inflammatory drug;
   (b) injecting a plurality of the microparticles into the skin of an immune-competent mammal;
   (c) imaging the mammal for cathepsin activity, reactive oxygen species, or a combination thereof;
   wherein a decrease in cathepsin activity, reactive oxygen species, or a combination thereof at the injection site compared to a control is an indication that the candidate anti-inflammatory drug is suitable to prevent fibrosis of encapsulated cells.

20. The method of claim 18, wherein the disease is diabetes.

21. The composition of claim 1, wherein the one or more anti-inflammatory drugs is selected from the group consisting of a steroidal anti-inflammatory drug, an mTOR inhibitor, a calcineurin inhibitor, and a synthetic or natural anti-inflammatory protein.

22. The composition of claim 1, wherein the one or more anti-inflammatory drugs are antiproliferative drugs selected from the group consisting of dexamethasone, 5-fluorouracil, daunomycin, paclitaxel, curcumin, resveratrol, and mitomycin.

23. The composition of claim 1, wherein the one or more anti-inflammatory drugs are selected from the group consisting of methylprednisolone, prednisolone, hydrocortisone, fludrocortisone, prednisone, celecoxib, ketorolac, piroxicam, diclorofenac, ibuprofen, and ketoprofen.

24. The composition of claim 1, wherein the one or more anti-inflammatory drugs is selected from the group consisting of a rapamycin, cyclosporin, and tacrolimus/FK-506.

* * * * *